(12) United States Patent
Tamiya et al.

(10) Patent No.: US 9,339,205 B2
(45) Date of Patent: May 17, 2016

(54) WAVEFORM ANALYZER AND WAVEFORM ANALYSIS METHOD

(75) Inventors: Yutaka Tamiya, Kawasaki (JP); Hiroaki Iwashita, Kawasaki (JP); Hiroyuki Higuchi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 1068 days.

(21) Appl. No.: 13/358,776

(22) Filed: Jan. 26, 2012

(65) Prior Publication Data

US 2012/0239328 A1    Sep. 20, 2012

(30) Foreign Application Priority Data

Mar. 18, 2011    (JP) .................................. 2011-060790

(51) Int. Cl.
| | |
|---|---|
| *A61B 5/0452* | (2006.01) |
| *A61B 5/0464* | (2006.01) |
| *G06K 9/00* | (2006.01) |
| *G01R 29/02* | (2006.01) |

(52) U.S. Cl.
CPC ........ *A61B 5/04525* (2013.01); *G06K 9/00536* (2013.01); *A61B 5/0464* (2013.01); *G01R 29/02* (2013.01)

(58) Field of Classification Search
CPC ........................ G06K 9/00536; A61B 5/04525
USPC .......................................................... 702/70
See application file for complete search history.

(56) References Cited

U.S. PATENT DOCUMENTS

2008/0063007 A1*  3/2008  Christiaens et al. .......... 370/458
2009/0287107 A1   11/2009  Beck-Nielsen et al.

FOREIGN PATENT DOCUMENTS

| JP | 6-46359 B | 6/1994 |
|---|---|---|
| JP | 2003-121472 A | 4/2003 |
| JP | 2006-67335 A | 3/2006 |
| JP | 2010-500052 A | 1/2010 |
| WO | WO-2007/144307 A2 | 12/2007 |

OTHER PUBLICATIONS

Ge et al., "Cardiac arrhythmia classification using autoregressive modeling", 2002, BioMedical Engineering OnLine 2002, 1:5, pp. 1-12.*

Willis Tompkins, "Biomedical Digital Signal Processing", 2000, previously printed by Prentice Hall, pp. 271-272.*

(Continued)

*Primary Examiner* — Regis Betsch
(74) *Attorney, Agent, or Firm* — Fujitsu Patent Center

(57) ABSTRACT

A waveform analyzer includes a converter which converts a logical function, where a pair of data including a time and a value at the time is variable, created according to data sets of a time and a value of a signal waveform at the time into a second function expressed by a binary decision diagram, an acquisition unit which obtains for each of characteristic points of a reference waveform a condition representative of constraints on a relationship between time information specified by the points and a value corresponding to the time information in the signal waveform according to a value of the reference waveform at the points and a specified tolerance given to a value of the reference waveform, and a searching unit which applies the condition for each of the points to the second function to obtain a time range which meets the entirety of the conditions.

12 Claims, 20 Drawing Sheets

(56) References Cited

OTHER PUBLICATIONS

Barni et al., "Secure Evaluation of Private Linear Branching Programs with Medical Applications",2009, ESORICS 2009 paper, https://eprint.iacr.org/2009/195.pdf.*

Acharya et al., "Advances in Cardiac Signal Processing", 2007, Chapter 8, Springer-Verlag Berlin Heidelberg, pp. 209-226.*

Frank Pfenning, "Lecture Notes on Binary Decision Diagrams", Oct. 2010, pp. 1-15; https://www.cs.cmu.edu/~fp/courses/15122-f10/lectures/19-bdds.pdf.*

Bryant, Randal E. "Graph-Based Algorithms for Boolean Function Manipulation", IEEE Transactions on Computers, C-35(8):677-691, Aug. 1986.

* cited by examiner

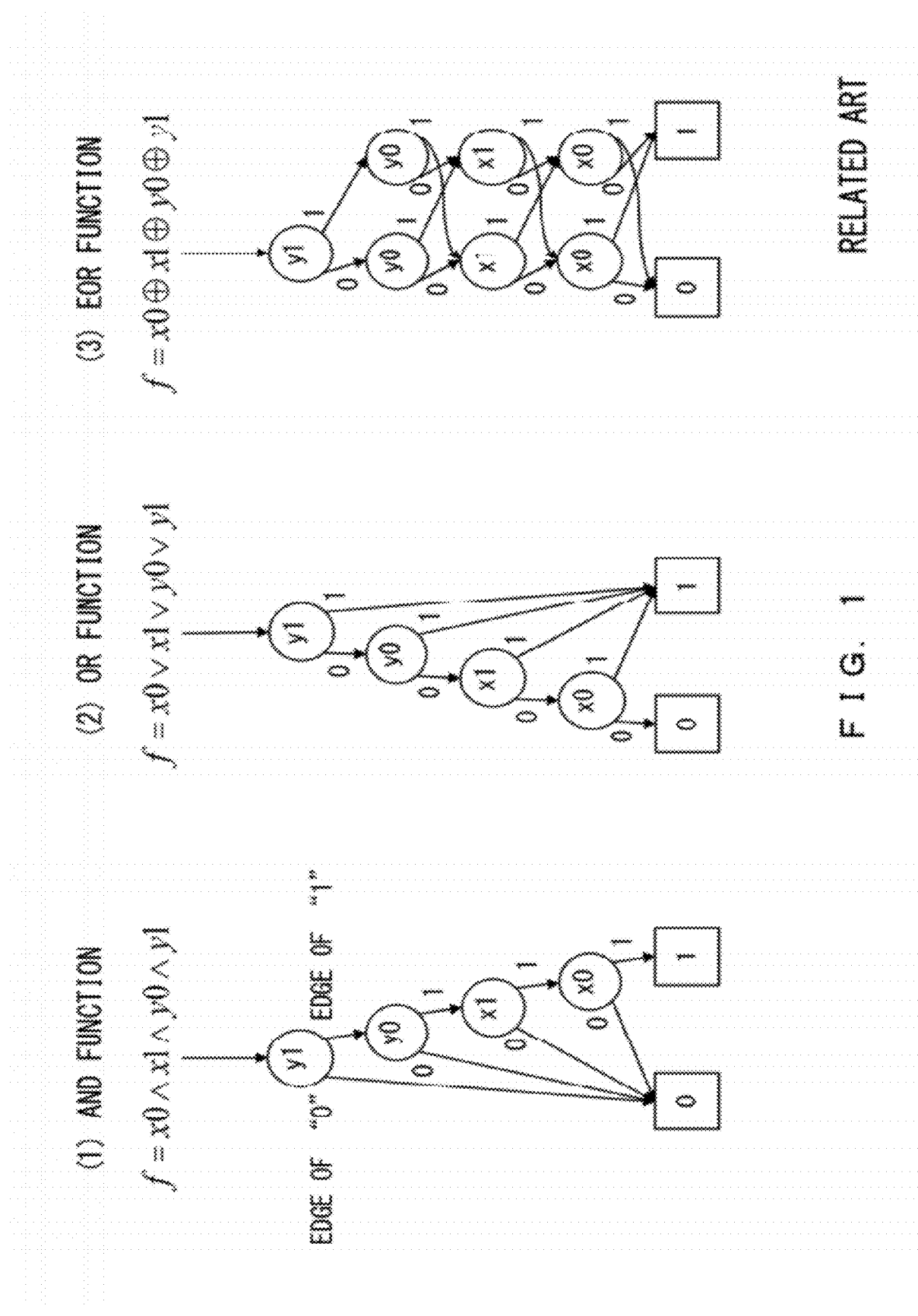

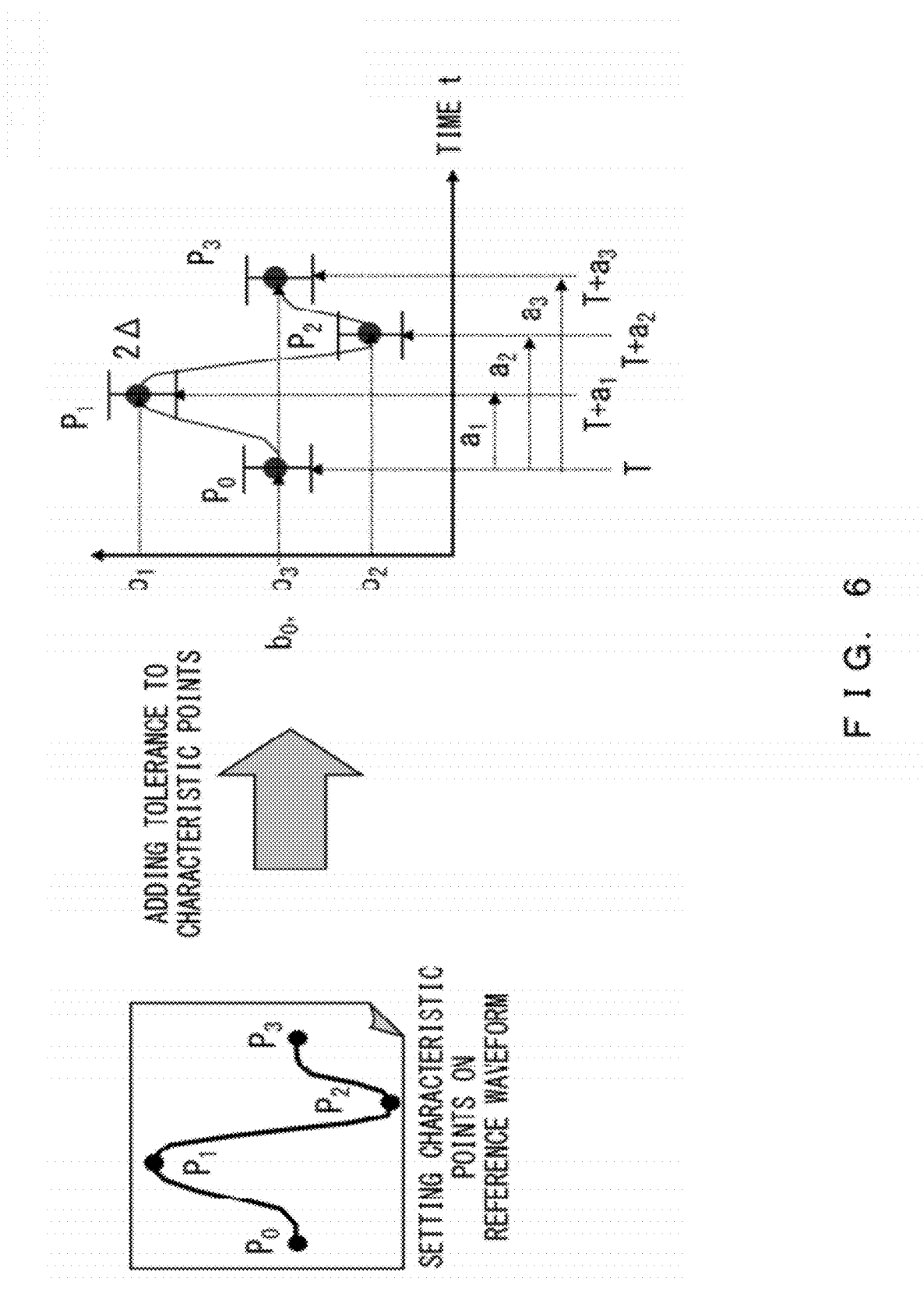
F I G. 6

F I G. 8

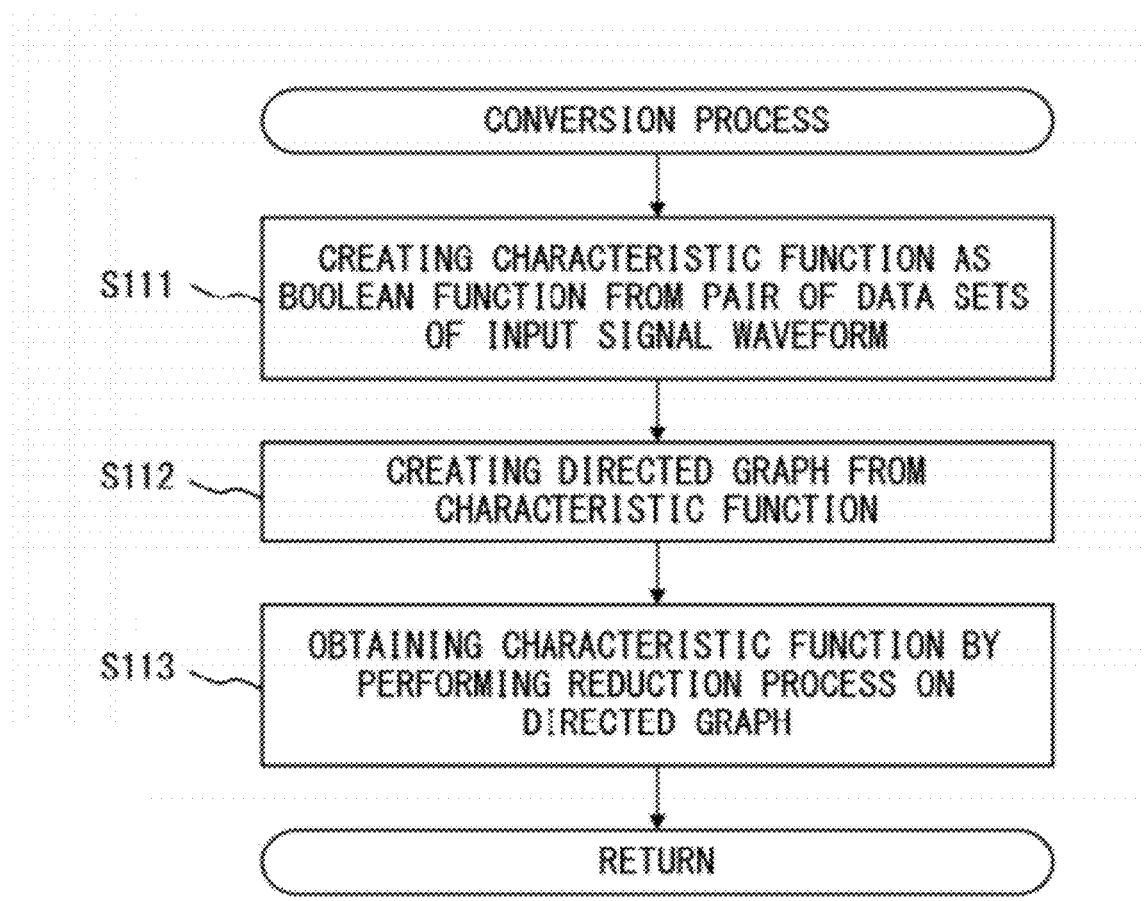
F I G. 1 1

WAVEFORM ANALYZER AND WAVEFORM ANALYSIS METHOD

CROSS-REFERENCE TO RELATED APPLICATION

This application is based upon and claims the benefit of priority of the prior Japanese Patent Application No. 2011-060790, filed on Mar. 18, 2011, the entire contents of which are incorporated herein by reference.

FIELD

The embodiments discussed herein are related to the technique for searching waveform.

BACKGROUND

In the field of medical care or health care, a large amount of signal data is collected from moment to moment by various types of sensors such as blood pressure sensors and electrocardiogram sensors which obtain biometric information. By quickly and accurately searching for the necessary information from the large amount of signal data, physical abnormalities can be detected without delay.

However, there is wide variety of information to be searched for depending on the types of signal data to be searched. For example, from electrocardiogram data, it is an object to detect the heart rate or the existence of arrhythmia. Further, more accurate diagnosis becomes possible by searching for target information by repetitively altering the search condition in a variety of ways.

As one of such techniques, pattern matching is known. Pattern matching is a technique for searching for and extracting a portion of the preliminarily set reference waveform and a portion of the shape of waveform that are similar from the signal waveform in a time series obtained by a sensor.

Some techniques related to the pattern matching are known.

For example, as a first technique of pattern matching, a technique is known in which pattern matching is performed by executing a logical operation between a logical value of emission/non-emission of light at an indicator which indicates the pixel of a signal waveform and a logical value of the setting data of the reference waveform set on the display of the indicator.

Moreover, for example, as a second technique, a technique is known in which matching is performed between a characteristic parameter of voice obtained by converting a voice signal into a frequency spectrum and a characteristic parameter of a registered standard voice.

Moreover, for example, as a third technique, a technique is known in which the identification of voice information included in two signals is performed by comparing the frequency information extracted from the two signals so as not to be affected by a phase shift or signal delay.

In such techniques for pattern matching, the search of waveform data in the direction of the axis of value (the direction of data value) is sequentially performed in a time series. Such a data search performed in the direction of the axis of value generally has a low flexibility and a low process efficiency. When pattern matching is repeatedly performed by altering several types of reference patterns, it is necessary to read the waveform data again every time the pattern matching is repeated. Accordingly, process efficiency tends to be low in such cases regarding both the operational efficiency and the capacity of the memory required to perform the process.

Incidentally, a technique has been proposed for applying a Binary Decision Tree to the algorithm of determining whether or not a specified pattern exists in a electroencephalogram signal.

Moreover, a binary decision diagram (BDD) is known as another background art. A BDD is a data structure for efficiently representing a logical function (Boolean function), which was proposed by Randal E. Bryant.

A BDD is a directed acyclic graph consisting of nodes representing the constant of "0" or "1", nodes to which variables are given (variable nodes), and edges connecting the variable node and the other nodes. Here, each of the variable nodes has the edges of "0" and "1", and depending on whether the value given to a variable node is "0" or "1", the node at the lower-order level (the depth from the root nodes of the decision tree) is selected. The last arrived constant node in consequence of the repeated selection indicates the value of a logical function in the BDD, where the value of the gone-through edges is substituted for the variable given to the variable node.

Moreover, a BDD is defined as [1] being a binary decision tree, [2] having ordered variables, and [3] having been reduced. Accordingly, a BDD should be referred to as a ROBDD (Reduced Ordered BDD) to be exact. However, when "BDD" is referred to, it generally indicates "ROBDD".

FIG. 1 is a diagram in which basic logical functions are represented by using a BDD. Here, (1) is the AND function where the AND of variables x0, x1, y0, and y1 are output. Moreover, (2) is the OR function where the OR of variable x0, x1, y0, and y1 are output. Furthermore, (3) is the exclusive-OR (EOR) function where the exclusive-OR of variables x0, x1, y0, and y1 are output.

A BDD involves the following features: [1] a logical function can be represented in a compact manner, [2] the calculation among logical functions can be performed efficiently, and [3] the BDD expression can be uniquely determined for a logical function (canonicality).

Note that the techniques disclosed in the following documents are known.
Document 1:
  Japanese Laid-open Patent Publication No. 2003-121472
Document 2:
  Japanese Examined Patent Application Publication No. H06-046359
Document 3:
  Japanese Laid-open Patent Publication No. 2006-067335
Document 4:
  Japanese National Publication of International Patent Application No. 2010-500052
Document 5:
  Randal E. Bryant, "Graph-Based Algorithms for Boolean Function Manipulation", IEEE Transactions on Computers, Vol. C-35(8), pp. 677-691, August 1986

SUMMARY

According to an aspect of the embodiment, a waveform analyzer which searches a signal waveform of an input signal for a portion similar to a reference waveform, the waveform analyzer includes a signal waveform obtaining unit which obtains a pair of data sets of a time and a value of the signal waveform at the time obtained by sampling the signal waveform, a converter which creates according to the pair of data sets a characteristic function which is a logical function where a pair of data including a time and a value at the time is variable, and which converts the created characteristic function into a second function which is an expression on a binary decision diagram, a constraint condition acquisition unit which obtains for each of characteristic points of the reference waveform a constraint condition representative of constraints on a relationship between time information specified by the characteristic points and a value corresponding to the time information in the signal waveform according to a value of the reference waveform at the characteristic points and a specified tolerance given to a value of the reference waveform, and a searching unit which applies the constraint condition for each of the plurality of characteristic points to the second function to obtain a time range which meets the constraint condition for all the plurality of characteristic points, and which outputs information of the time range as a result of a search.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

BRIEF DESCRIPTION OF DRAWINGS

FIG. 1 is a diagram in which basic logical functions are represented by using a BDD.

FIG. 6 is a diagram illustrating a method for obtaining a constraint condition.

FIG. 8 illustrates an example of a program which allows a computer to perform the processes of a searching unit.

FIG. 11 is a flowchart illustrating how a conversion process is performed.

DESCRIPTION OF EMBODIMENTS

Preferred embodiments of the present invention will be explained with reference to accompanying drawings.

Figure 2:
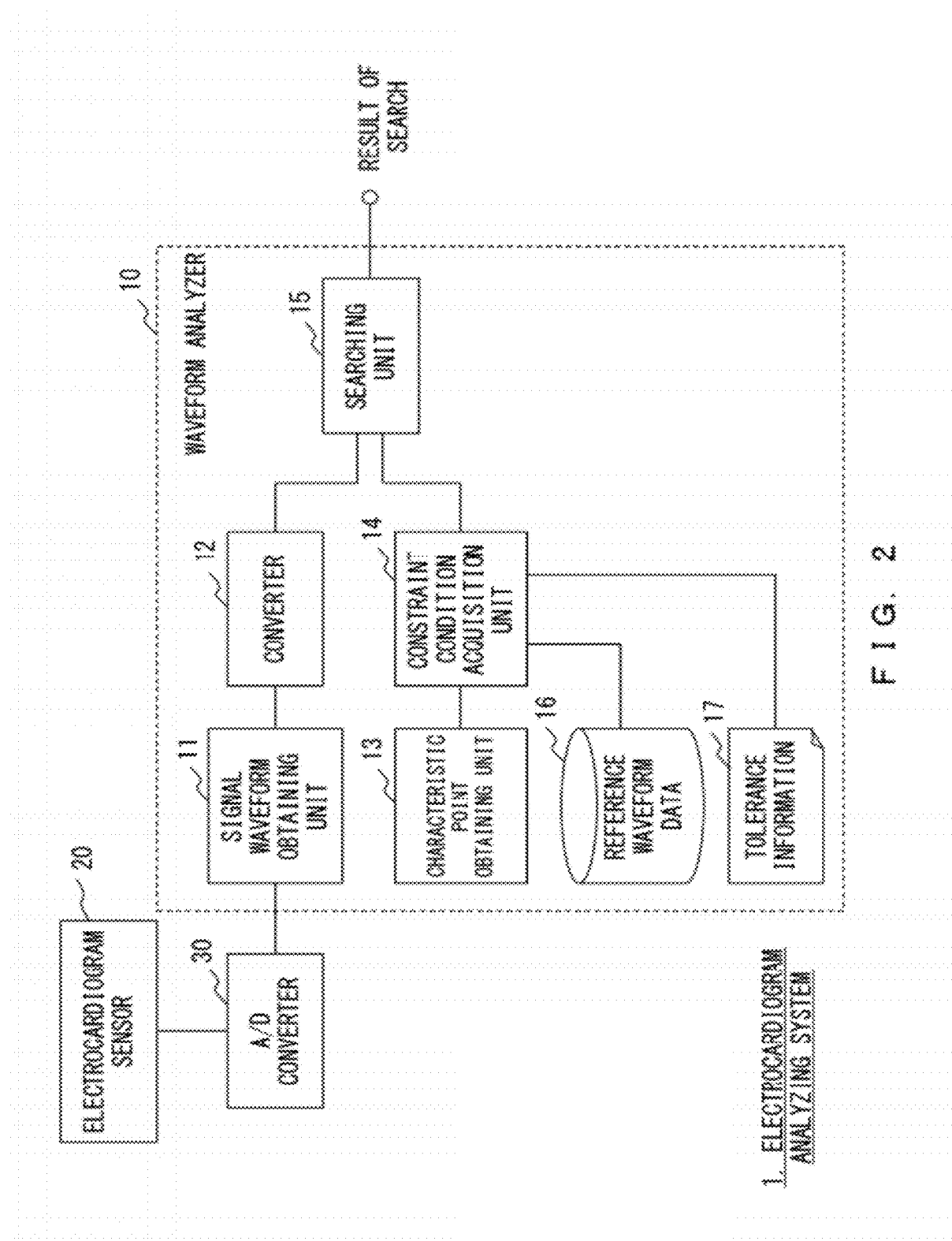
FIG. 2 is a functional block diagram of an electrocardiogram analyzing system including a waveform analyzer.
Figure 3:
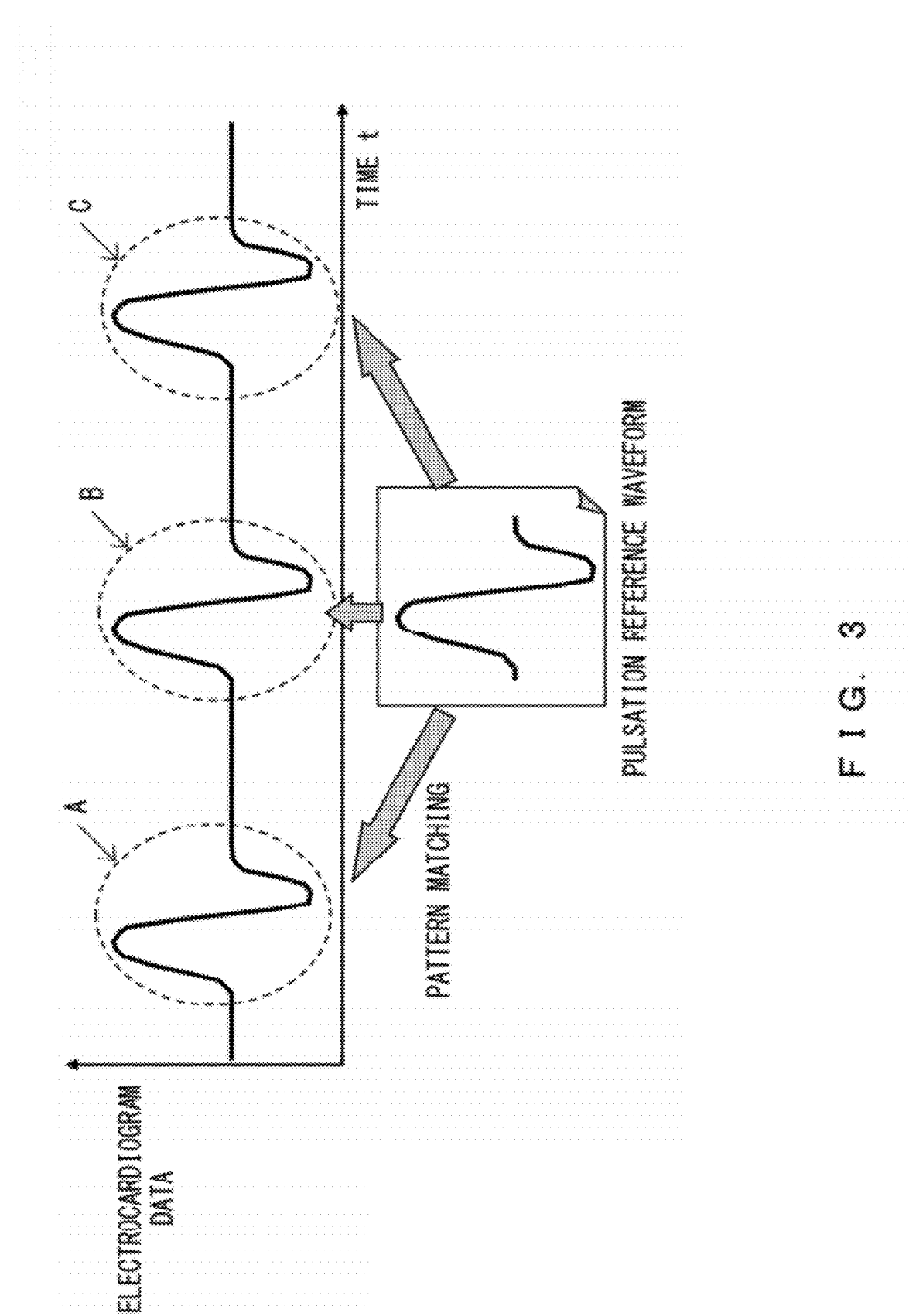
FIG. 3 is a diagram illustrating the functions of an electrocardiogram analyzing system.
Figure 4:
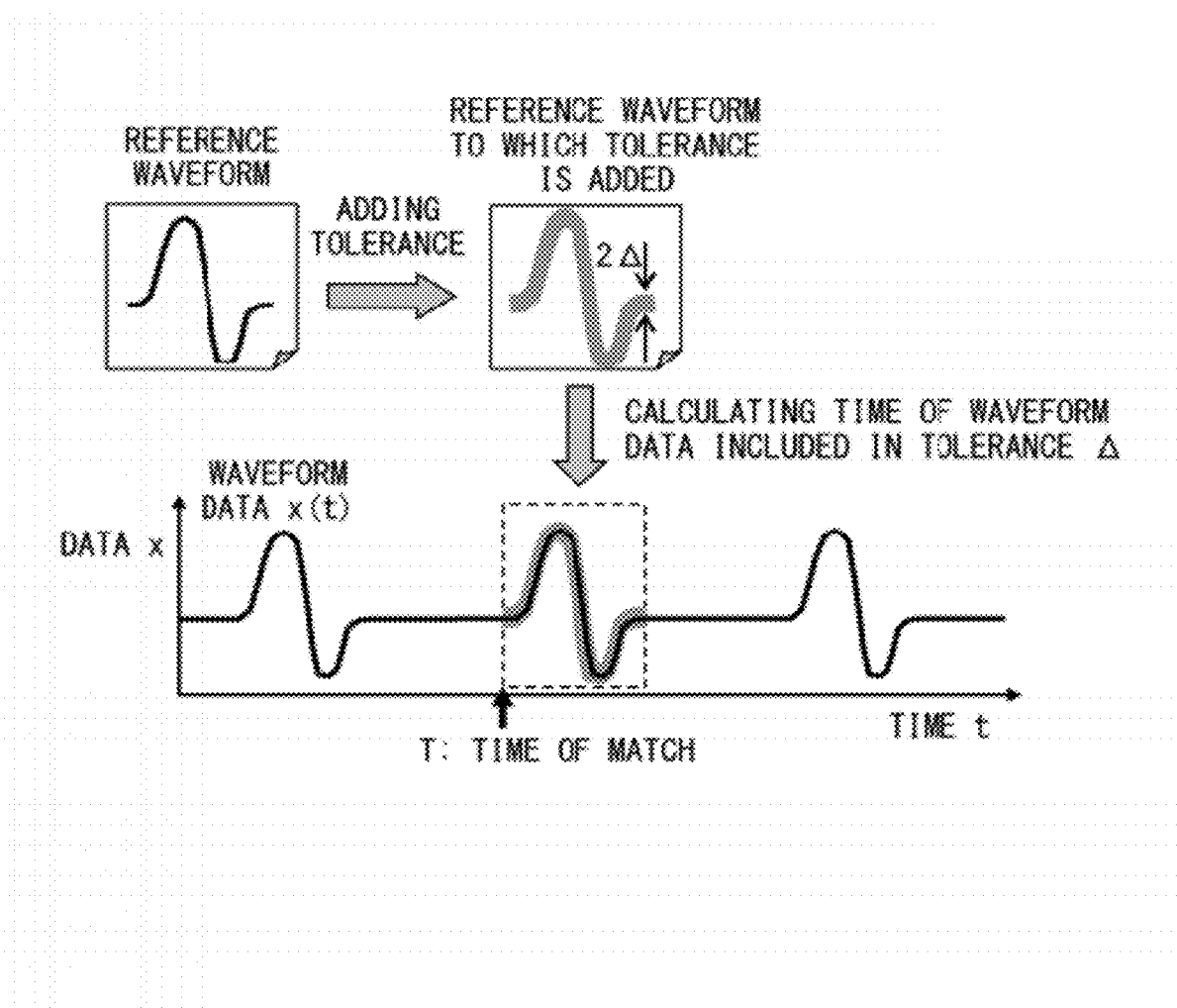
FIG. 4 is a diagram illustrating the general outlines of the operation of a waveform analyzer.

Firstly, FIGS. 2, 3, and 4 will be described. FIG. 2 is a functional block diagram of an electrocardiogram analyzing system including a waveform analyzer. Moreover, FIG. 3 is a diagram illustrating the functions of the electrocardiogram analyzing system, and FIG. 4 is a diagram illustrating the general outlines of the operation of the waveform analyzer included in the electrocardiogram analyzing system.

An electrocardiogram analyzing system 1 performs pattern matching between the observed electrocardiogram data and the preliminarily provided pulsation reference waveform to search the electrocardiogram data for a similar portion between the electrocardiogram data and the pulsation reference waveform. In the example of FIG. 3, the electrocardiogram analyzing system 1 extracts a total of three portions A, B, and C, which are circled by broken lines given to the electrocardiogram data, as portions similar to the pulsation reference waveform.

As illustrated in FIG. 2, the electrocardiogram analyzing system 1 includes a waveform analyzer 10, an electrocardiogram sensor 20, and an A/D converter 30.

The waveform analyzer 10 searches the signal waveform of an input signal for portions similar to the reference waveform. As illustrated in FIG. 4, the waveform analyzer 10 searches the signal waveform of an input signal for a portion included in the reference waveform to which tolerance is added, and outputs the information of time which specifies the position of the portion on the signal waveform.

The electrocardiogram sensor 20 measures the action potential of cardiac muscle, and outputs an electrocardiogram signal.

The A/D converter 30 is an analog-digital converter which samples an electrocardiogram signal output from the electrocardiogram sensor 20 and outputs a pair of data sets, which express the electrocardiogram waveform, consisting of the paired data of a time and the value of the electrocardiogram signal at that time. The pair of data sets output from the A/D converter 30 is input to the waveform analyzer 10.

In FIG. 2, the A/D converter 30 is illustrated as an element independent from both the waveform analyzer 10 and the electrocardiogram sensor 20. However, the waveform analyzer 10 or the electrocardiogram sensor 20 may include the A/D converter 30.

Next, the functional blocks provided by the waveform analyzer 10 will be described.

The waveform analyzer 10 includes a signal waveform obtaining unit 11, a converter 12, a characteristic point obtaining unit 13, a constraint condition acquisition unit 14, and a searching unit 15. Furthermore, reference waveform data 16 and tolerance information 17 are preliminarily stored in the waveform analyzer 10.

The reference waveform data 16 is the waveform data which indicates the reference waveform, and is the waveform data of the above-described pulsation reference waveform in FIG. 3.

The tolerance information 17 is the information about the allowable range in cases where it is determined, in the result of searching a similar portion between the signal waveform of an input signal and the reference waveform, that the two waveforms are similar.

In the present embodiment, the reference waveform data 16 and the tolerance information 17 are preliminarily stored in the waveform analyzer 10. However, the waveform analyzer 10 may include a storage unit to store these pieces of externally input data in the storage unit.

The signal waveform obtaining unit 11 obtains a pair of data sets which includes the paired data of a time obtained by sampling the signal waveform and a value of the signal waveform at that time. In the configuration of FIG. 2, the signal waveform obtaining unit 11 obtains the above-described pair of data sets indicating the electrocardiogram waveform, which is output from the A/D converter 30.

The converter 12 generates according to the above-described pair of data sets a characteristic function which is a logical function where the paired data of a time and a value at that time is variable, converts the generated characteristic function into a second function which is an expression on the above-described binary decision diagram (BDD), and then outputs the second function. In the configuration of FIG. 2, the converter 12 generates according to the pair of data sets obtained by the signal waveform obtaining unit 11 a characteristic function representing the above-described electrocardiogram waveform where the paired data of a time and a value at that time is variable, converts the generated characteristic function into a second function which is an expression on the BDD, and then outputs the second function.

The characteristic point obtaining unit 13 obtains setting instructions for a plurality of characteristic points which are set on the reference waveform expressed in the reference waveform data 16.

For each of the characteristic points obtained by the characteristic point obtaining unit 13, the constraint condition acquisition unit 14 obtains the constraint condition representative of the constraints on the relationship between the time information specified by the characteristic points and a value corresponding to the time information in the above-described signal waveform. The constraint condition acquisition unit 14 acquires the constraint condition according to a value of the reference waveform at the characteristic points and the specified tolerance given to the value of the reference waveform.

The searching unit 15 firstly applies the constraint condition acquired by the constraint condition acquisition unit 14 for each of the characteristic points to the above-described converted second function (characteristic function expressed in the BDD) to obtain the time range which meets the constraint condition for all the characteristic points. Then, the searching unit 15 outputs the information of the time range as a search result of the waveform analyzer 10.

The details will be described later, but in the waveform analyzer 10 as configured above, the signal waveform of an input signal is expressed in a BDD, thereby reducing the amount of data required for the expression and contributing to the reduction in capacity of a memory required for waveform analysis. Moreover, as the pattern matching between the signal waveform of an input signal and the reference waveform is performed by the computation on a BDD, a high efficiency in computation is achieved. As described above, the waveform analyzer 10 of FIG. 2 provides highly efficient pattern matching.

The searching unit 15 of FIG. 2 may be configured to calculate the time which meets the constraint condition for each of the above-described characteristic points, for example, as follows. That is, the searching unit 15 firstly performs for each of the characteristic points a variable replacement operation, which corresponds to the time difference between the time specified by the characteristic points and the reference time preliminarily set for the reference waveform, on the above-described second function. Then, the searching unit 15 applies the above-described constraint condition obtained for the characteristic points to the characteristic function on which the variable replacement operation is performed to calculate the time range which meets the constraint condition for the characteristic points.

Alternatively, the searching unit 15 of FIG. 2 may for example be configured to calculate the above-described time which meets the constraint condition for each of the characteristic points as follows. That is, the searching unit 15 firstly applies for each of the above-described characteristic points the constraint condition obtained for each of the characteristic points to the above-described second function. Then, the searching unit 15 performs a variable replacement operation, which corresponds to the time difference between the time specified by the characteristic points and the reference time preliminarily set for the reference waveform, on the time range which meets the constraint condition.

As described above, if the constraint condition is applied to the characteristic function expressed in the BDD before the variable replacement operation which corresponds to the time difference, the size of the BDD is reduced. Accordingly, a reduction in the amount of computation in the variable replacement operation is expected.

Moreover, the converter 12 of FIG. 2 creates, for example, a function as follows as a characteristic function. That is, the converter 12 creates a function where the elements of the above-described paired data are expressed in binary and the values of the levels are variable. Here, in this function, the value "1" is returned when the value included in the above-described pair of data sets corresponds to the value of the variable, and the value "0" is returned when a value not included in the above-described pair of data sets corresponds to the value of the variable.

As will be described later in detail, if such a function is created as a characteristic function, it is possible to convert the characteristic function into an expression on a BDD.

Moreover, the constraint condition acquisition unit 14 of FIG. 2 may be configured, for example, to create a BDD representing the constraint condition according to the value of the reference waveform at the characteristic points and the specified tolerance. At this time, the searching unit 15 applies the constraint condition to the characteristic function by performing an AND operation between the above-described second function and a BDD representing the constraint condition.

As described above, if the constraint condition is expressed in a BDD, it is possible to apply the constraint condition to the characteristic function in the logical operation on the BDD. Accordingly, the operational efficiency for the application improves, and as a result, the efficiency in the process of pattern matching further improves.

Here, the constraint condition may represent, for example, constraints on the maximum value of the signal waveform in the specified period around the time specified by the characteristic point. Moreover, the constraint condition may represent, for example, constraints on the minimum value of the signal waveform in the specified period around the time specified by the characteristic point. Furthermore, the constraint condition may represent, for example, constraints on the average value of the signal waveform in the specified period around the time specified by the characteristic point.

Next, some functions provided by the functional blocks of the waveform analyzer 10 will be further described in detail.

Firstly, a method for creating a characteristic function according to a pair of data sets obtained by the signal waveform obtaining unit 11 by using the converter 12 and a method for conversion into the created characteristic function into the expression on a BDD by using the converter 12 will be described.

Firstly, the converter 12 defines characteristic function $f(t, x)$ where a pair of a time t and a value x at the time $t(t, x)$ is a variable. The function $f(t, x)$ is defined to return the value "1" when $(t, x)$ is the pair of values received from the signal waveform obtaining unit 11, i.e., when $(t, x)$ indicates a point on the signal waveform of the input signal ("electrocardiogram" in the present embodiment), and is defined to return the value "0" in the other cases. If the function ƒ(t, x) is defined as above, it can be seen that the set (t, x) satisfying "f(t, x)=1" indicates the signal waveform of an input signal.

At this time, the converter 12 expresses the variables of the characteristic function f(t, x), i.e., the time t and the value x, by using a binary (binary number), and generates the characteristic function f(t, x) as a Boolean function where the values of columns are variables. In other words, the converter 12 generates the Boolean function f(tn−1, tn−2, ..., t1, t0, xm−1, xm−2, ..., x1, x0), where the time t is expressed by n-levels of binary as a Boolean variable of n-bit, and the value x is expressed by m-levels of binary as a Boolean variable of m-bit, as expressed in Equation 1 below.

$$t = (t_{n-1}, t_{n-2}, \ldots, t_1, t_0,), \text{ where } t = \sum_{i=0}^{n-1} 2^i \times t_i$$

$$x = (x_{m-1}, x_{m-2}, \ldots, x_1, x_0,), \text{ where } x = \sum_{j=0}^{m-1} 2^j \times x_j$$

Equation 1

If the signal waveform of an input signal is expressed as such a characteristic function, it is possible for the characteristic function to be converted to an expression on a BDD. The conversion of the characteristic function into an expression on a BDD will be described with reference to FIGS. 5A, 5B, and 5C.

Figure 5A:
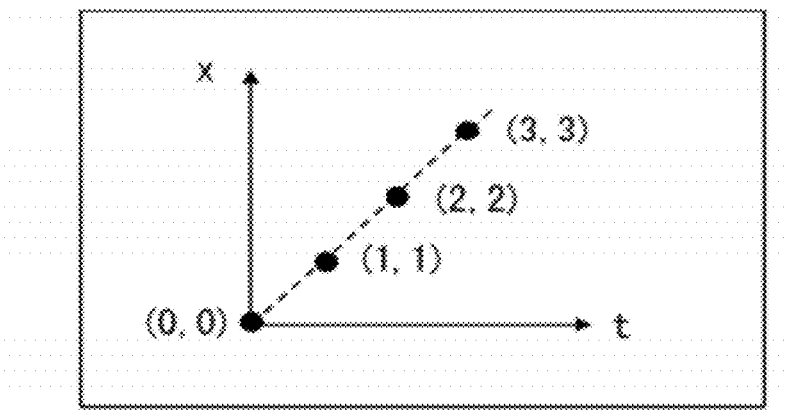
FIG. 5A is a diagram (1) illustrating a method for converting a characteristic function into an expression on a BDD.

FIG. 5A illustrates an example signal waveform of "x=t". It is assumed that the signal waveform is sampled and (t, x)={(0, 0), (1, 1), (2, 2), (3, 3)} are obtained for (t, x) of the time t and the value x.

Figure 5B:
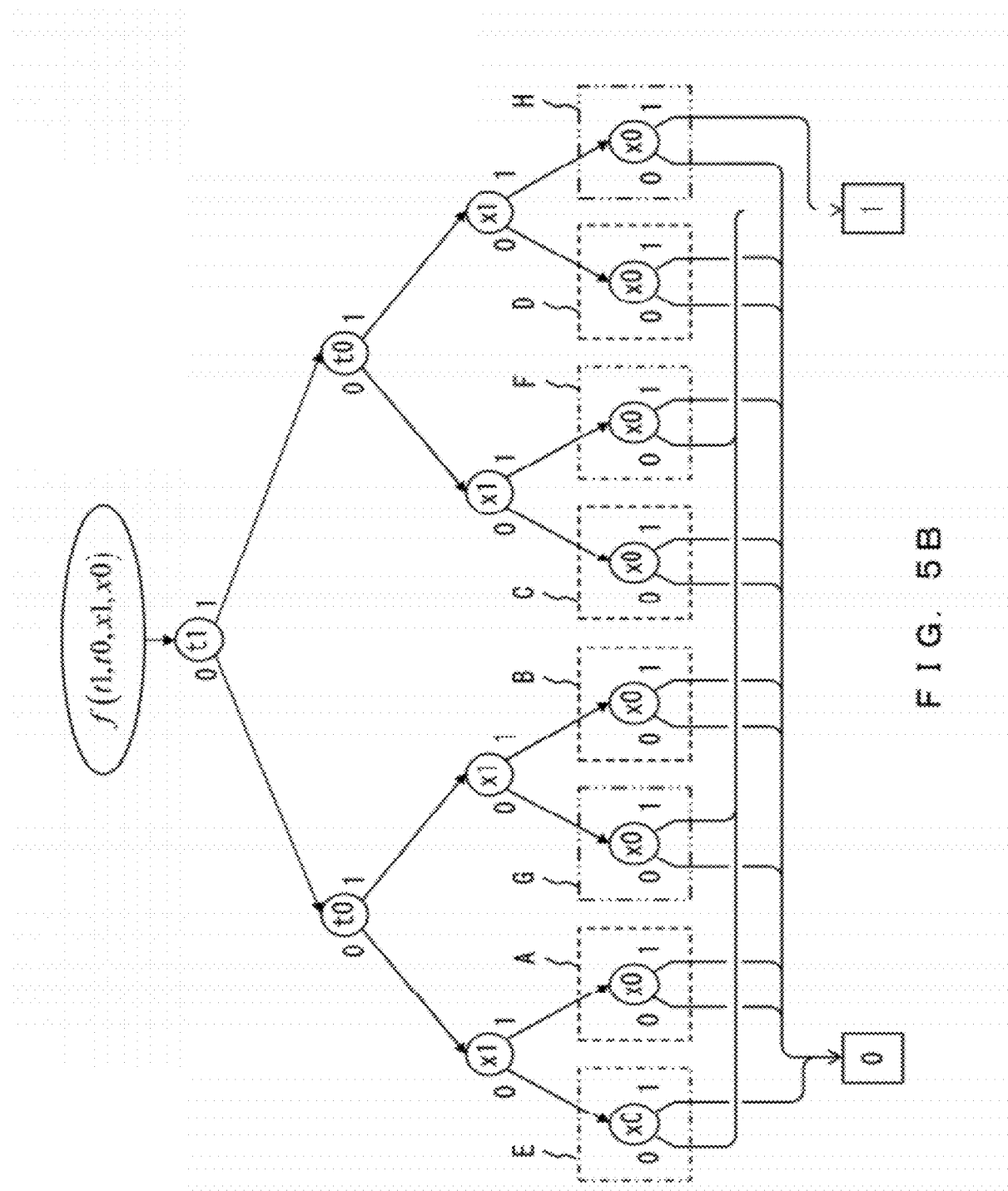
FIG. 5B is a diagram (2) illustrating a method for converting a characteristic function into an expression on a BDD.

When the time t and the value x are expressed in binary (a binary number), (t, x) becomes (t1, t0, x1, x0)={(0, 0, 0, 0), (0, 1, 0, 1), (1, 0, 1, 0), (1, 1, 1, 1)}. The characteristic function f(t1, t0, x1, x0) returns the value "1" only when one of the values is a variable, and returns the value "0" in the other cases. FIG. 5B represents this characteristic function by using a directed graph.

The structure of the directed graph may be expressed by using, for example, node data or a node table. The node data includes the information of labels for distinguishing the variables assigned to the nodes, and the information of pointers for pointing toward the node data of other nodes to which the edges of "0" and "1" of the nodes are directed. The node table is a table where the information of the assigned variables and the information of other nodes to which the edges of "0" and "1" of the nodes are directed are associated with each other for each node.

Next, a reduction process is performed on the directed graph of FIG. 5B. The following two rules of [1] and [2] are applied to the reduction process.

[1] Elimination of Redundant Node: In the graph of FIG. 5B, the destination node of the variable nodes A, B, C, and D in the box using broken lines is the same (here, the node of constant "0") regardless of whether the edge of "0" or "1" of the nodes is selected. Due to the reduction process, these variable nodes (such nodes are referred to as a "redundant node" or the like) are eliminated.

[2] Unification of Equivalent Variable Nodes: In the graph of FIG. 5B, the destination node of the variable nodes E and F in the box using alternate long and short dashed lines is the same (here, the node of constant "1") when the edge of "0" is selected, and is the same (here, the node of constant "0") when the edge of "1" is selected. Due to the reduction process, these variable nodes (such nodes are referred to as "equivalent variable nodes" or the like) E and F are unified.

In the graph of FIG. 5B, as the variable nodes G and H in the box using double short single long dashed lines are also equivalent to each other, and these two variable nodes G and H are also unified by the reduction process.

Figure 5C:
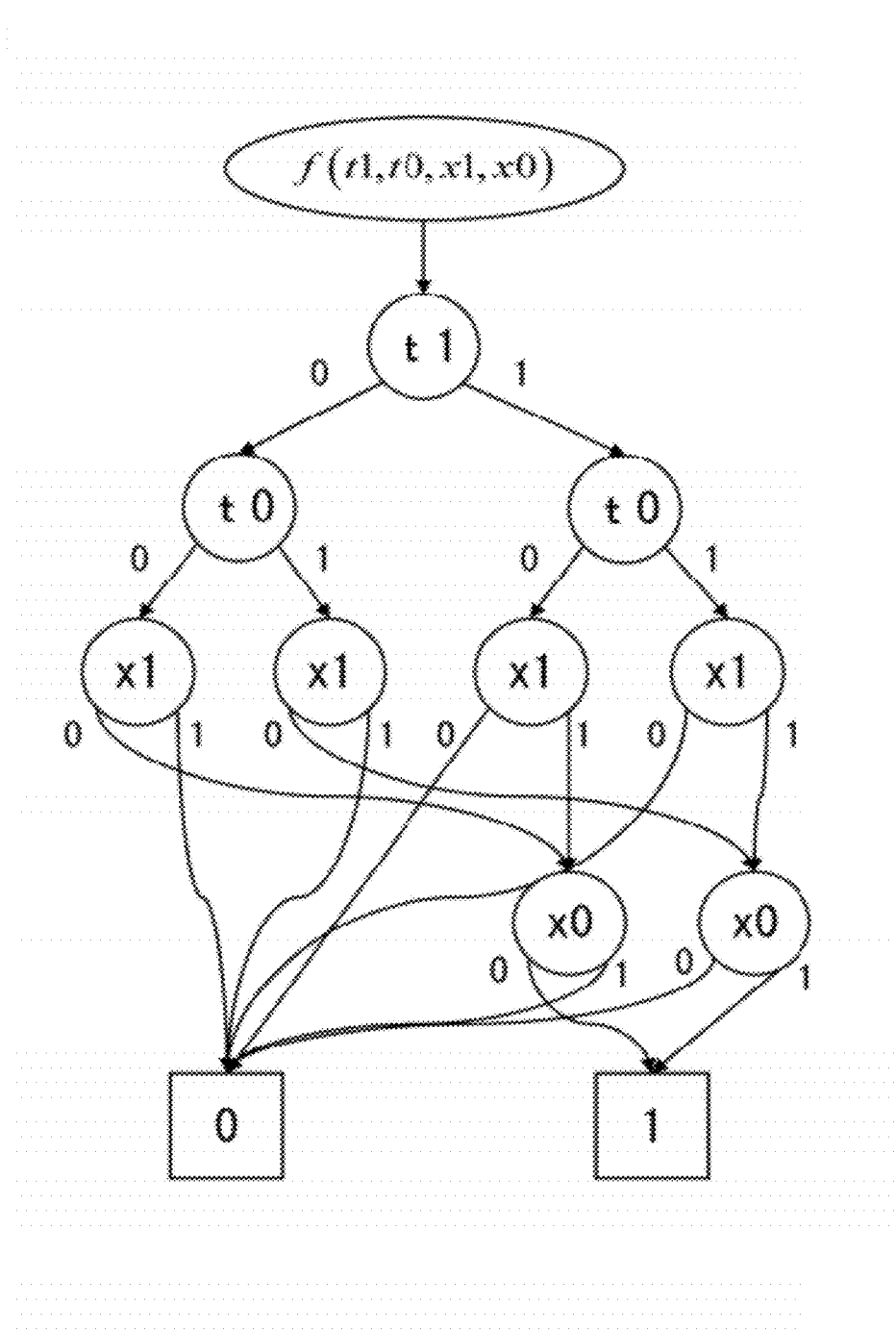
FIG. 5C is a diagram (3) illustrating a method for converting a characteristic function into an expression on a BDD.

In the graph of FIG. 5C, the expression of the characteristic function f(t1, t0, x1, x0), which is obtained by performing the reduction process to which the above-described two rules are applied on the graph of FIG. 5B, on a BDD is illustrated. It is seen that the characteristic function f(t1, t0, x1, x0) expressed in a BDD has a compact expression.

In the foregoing descriptions above, the method is described for firstly completing a directed graph of the characteristic function as illustrated in FIG. 5B and then performing a reduction process on the directed graph to obtain the BDD expression of characteristic function as illustrated in FIG. 5C. However, in practice, the creation of a directed graph of the characteristic function and its reduction process may be performed in parallel. In other words, referring to the above-described case, it may be configured such that every time a set of data (t1, t0, x1, x0) of the characteristic function f(t1, t0, x1, x0) is added to a being-created directed graph, a reduction process is performed on the directed graph to which the data is added. Accordingly, the capacity of the storage area for temporarily storing the data representing the directed graph of the characteristic function is reduced.

As described above, the converter 12 performs both the creation of a characteristic function according to a pair of data sets obtained by the signal waveform obtaining unit 11 and the conversion of the created characteristic function into the expression on a BDD (i.e., the above-described second function).

Next, a method for obtaining a constraint condition by using the constraint condition acquisition unit 14 will be described with reference to FIG. 6.

Firstly, an operator of the electrocardiogram analyzing system 1 of FIG. 2 sets a plurality of characteristic points on the reference waveform (i.e., the above-described pulsation reference waveform). In the setting, the start point, maximum point, minimum point, and end point or the like of the waveform which represents the shape characteristics of the reference waveform, for example the characteristic points P0, P1, P2, and P3 set on the reference waveform as illustrated in FIG. 6 on the left side, are selected as characteristic points. Note that all the reference waveform data 16 which represents the reference waveform may be set as characteristic points.

The characteristic point obtaining unit 13 obtains setting instructions on a plurality of characteristic points which are set on the reference waveform by the user as above, and passes the obtained setting instructions to the constraint condition acquisition unit 14. It is assumed that the passed characteristic points are Pi (i=0, 1, ..., k−1).

Once the characteristic point Pi is received, the constraint condition acquisition unit 14 obtains the elapsed time ai between the start time T and the time of the characteristic point Pi for each Pi, and the value bi on the reference waveform at the Pi. The waveform on the right side of FIG. 6 illustrates the elapsed time ai and the value bi of the reference waveform for each of the characteristic points P0, P1, P2, and P3 which are set on the reference waveform on the left side. Here, the characteristic point P0 is set to the start point of the reference waveform, and thus the elapsed time a0=0. For this reason, a0 is not indicated in the waveform on the right side of FIG. 6.

Next, the constraint condition acquisition unit 14 acquires the constraint condition Mi by allowing the tolerance information 17 for the values of the reference waveform bi at the characteristic points Pi. In other words, assuming that the tolerance information 17 has the value of $\Delta$, the constraint condition acquisition unit 14 acquires for each of the characteristic points Pi the range of the value of $bi \pm \Delta$ in which the elapsed time from the start time T of the reference waveform is ai as constraint condition Mi.

Next, a method for applying a constraint condition to the characteristic function expressed in the BDD (i.e., the above-described second function) by using the searching unit 15 will be described.

Figure 7:
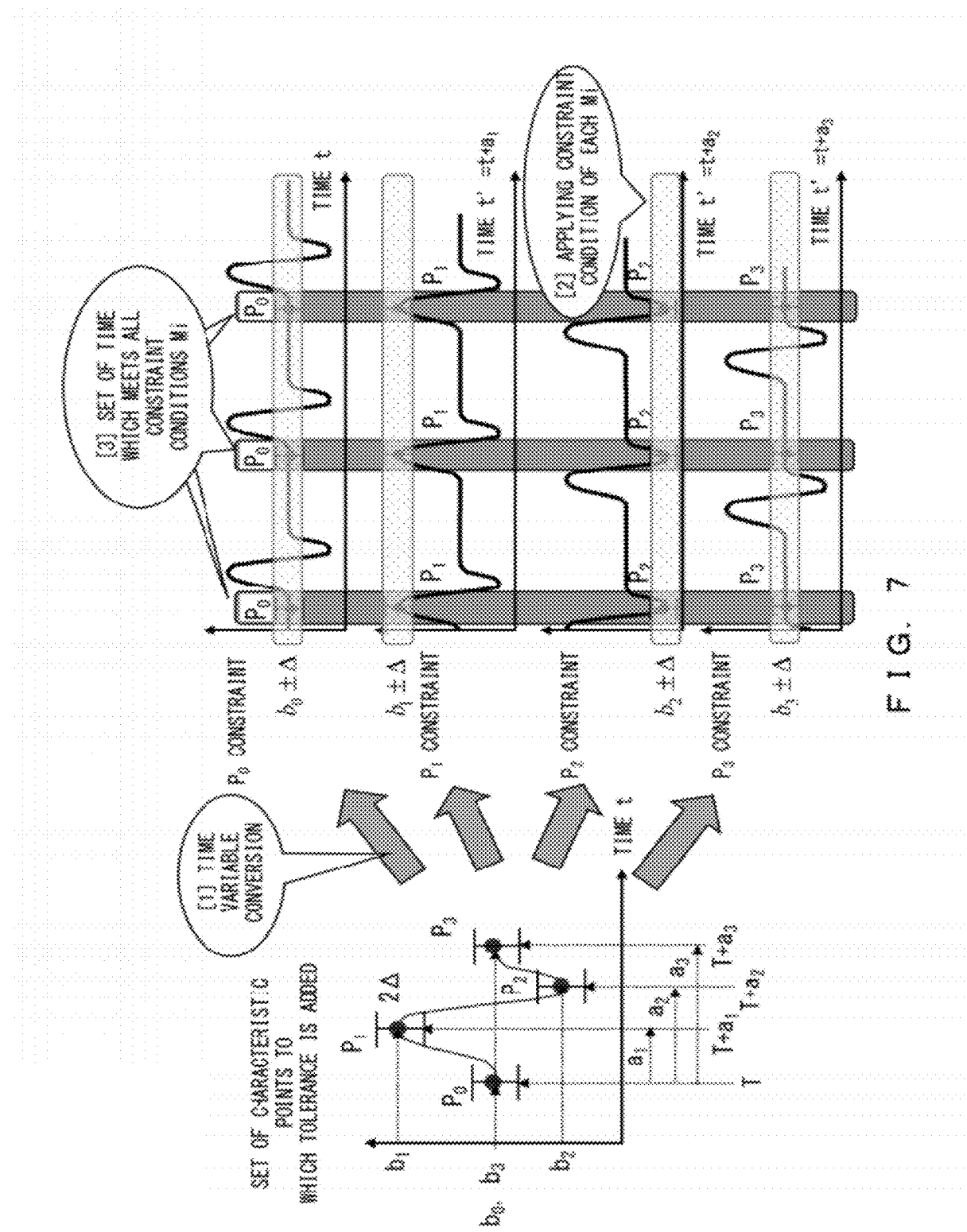
FIG. 7 is a diagram illustrating a method for applying a constraint condition to a characteristic function.

The searching unit 15 applies the constraint condition acquired by the constraint condition acquisition unit 14 Mi to the characteristic function expressed in the BDD one by one for each of the characteristic points Pi to obtain the time range which satisfies the entirety of the constraint conditions Mi. More specifically, the searching unit 15 obtains a search result by performing the processes of [1], [2], and [3] which are illustrated in FIG. 7, as follows.

[1] Firstly, the characteristic function expressed in the BDD $f(t, x)$ is converted by using the above-described elapsed time ai obtained for the characteristic point Pi to obtain the function $f'(t, x) = f(t+ai, x)$ in which the variable t of the time in the function is substituted with t+ai. The waveform expressed by the function $f'(t, x)$ in which the time variable is substituted as above is equivalent to what the original signal waveform of an input signal is moved in the direction of time axis by $-ai$.

[2] Next, the constraint condition Mi is applied to the $f'(t, x)$ to obtain the range of values that the variable t of the time may take (the set of times t at which $f'(t, x)=1$) in cases where the variable x takes a value within the range of $bi \pm \Delta$.

[3] The processes of [1] and [2] above are performed on each one of the characteristic points Pi, and according to a result of these processes, the range of the variable t of the time which meets the entirety of the constraint conditions Mi is obtained. Then, the obtained range of the time t is output as a search result of the waveform analyzer 10.

A program which allows a computer to perform the processes of [1], [2], and [3] can easily be made by using various types of general-purpose BDD packages which are widely open to the public.

Figure 8:
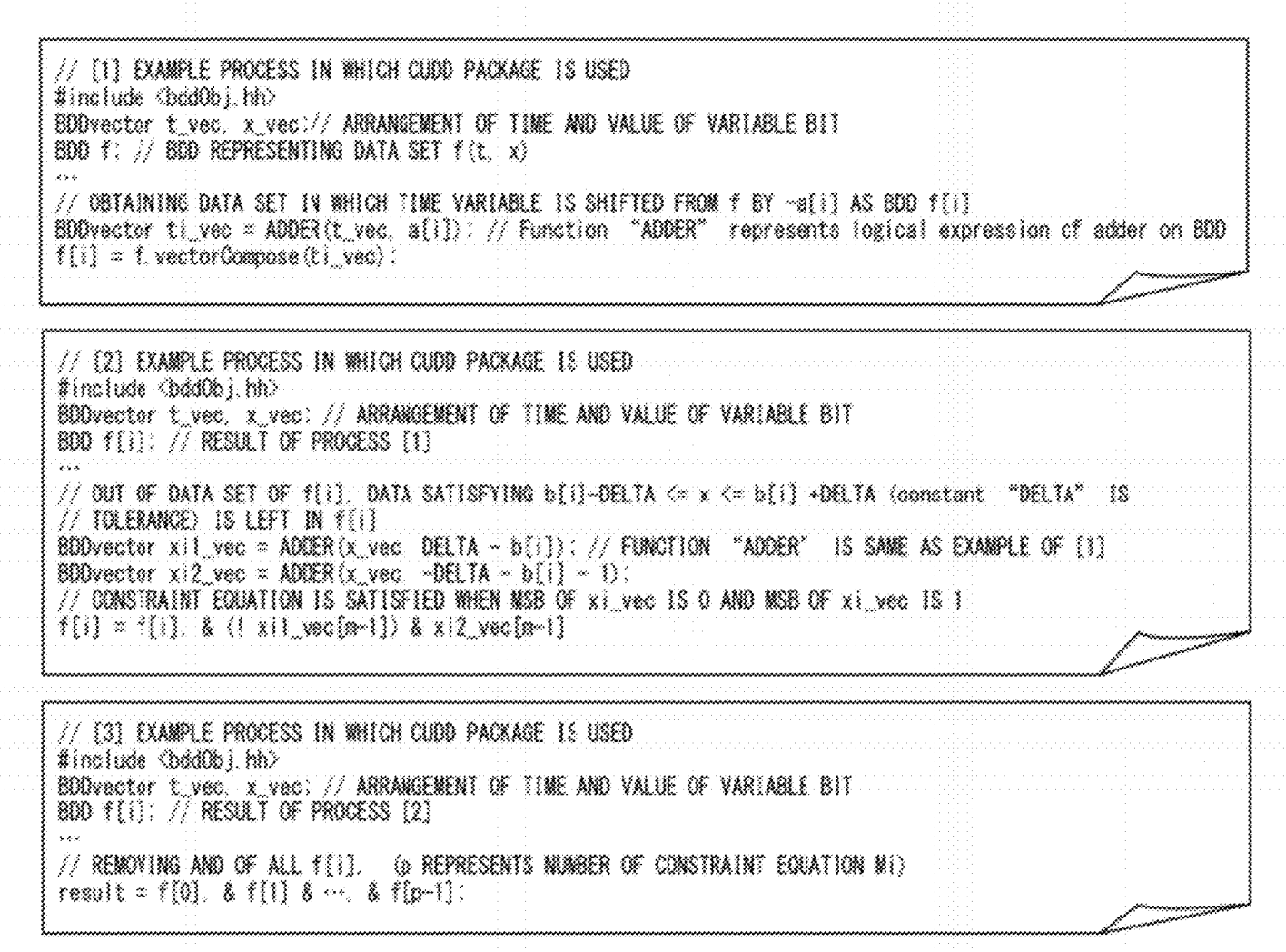

As an example of such a program, FIG. 8 illustrates a program for the above-described processes which is created by using C++ with the CUDD (Colorado University Decision Diagram Package), a BDD package published by the University of Colorado Boulder in the U.S., available on the Internet or the like. The program is described in the notes (comments described after "//") in FIG. 8.

The functional blocks provided for the waveform analyzer 10 provide the functions as described above.

The waveform analyzer 10 of FIG. 2 may be configured by using a standard computer.

Figure 9:
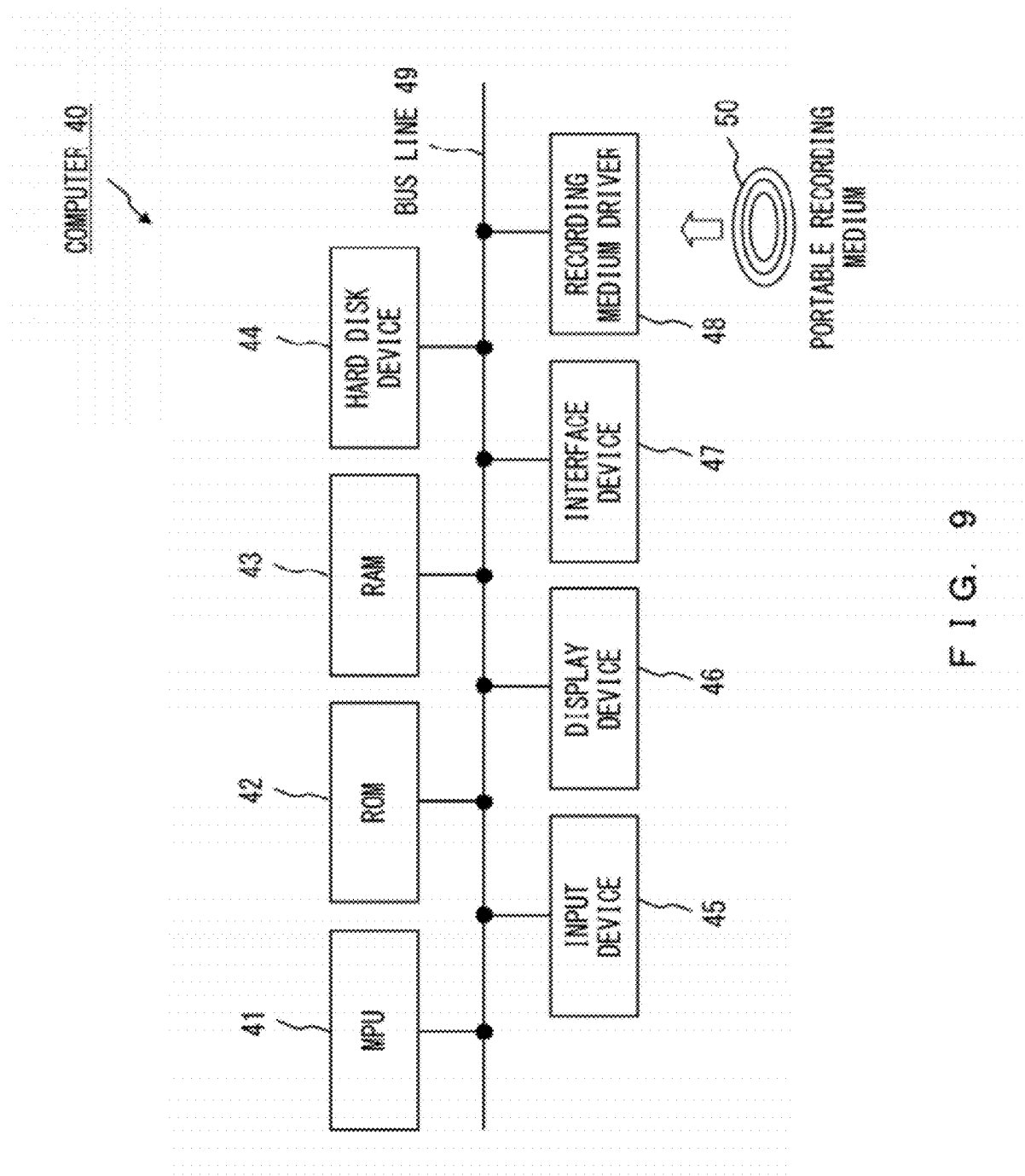
FIG. 9 is an example of the hardware configuration of a computer.

Here, FIG. 9 will be described. FIG. 9 illustrates an example of the hardware configuration of a computer which can function as the waveform analyzer 10.

A computer 40 includes an MPU 41, a ROM 42, a RAM 43, a hard disk device 44, an input device 45, a display device 46, an interface device 47, and a recording medium driver 48. These elements are connected to each other through a bus line 49, and various types of data can be transferred thereamong under the control of the MPU 41.

The MPU (Micro Processing Unit) 41 is a processor which controls the entire operation of the computer 40.

The ROM (Read Only Memory) 42 is a read-only semiconductor memory on which a specified basic control program is recorded. The MPU 41 reads and executes the basic control program during the start-up process of the computer 40, thereby enabling the operational control of the elements of the computer 40.

The RAM (Random Access Memory) 43 is a writable/readable semiconductor memory which is used as a working storage as necessary when the MPU 41 executes various types of control programs.

The hard disk device 44 is a storage device in which the various control programs executed by the MPU 41 or various types of data are stored. The MPU 41 executes the various types of control processes by reading and executing a specified control program stored in the hard disk device 44.

The input device 45 is, for example, a keyboard device or a mouse device. For example, when operated by an operator of the waveform analyzer 10, the input device 45 obtains the input of various types of information which is associated with the operation made by the operator, and transmits the obtained input information to the MPU 41.

The display device 46 is, for example, a liquid crystal display, and displays various types of texts and images according to the display data transmitted from the MPU 41.

The interface device 47 manages the transfer of various types of information among the various types of equipment connected to the computer 40.

The recording medium driver 48 reads various types of control programs or data which are recorded on the portable recording medium 50. The MPU 41 may be configured to read a specified control program recorded on the portable recording medium 50 through the recording medium driver 48 and execute the read control program to perform various types of control processes as will be described later. Moreover, the portable recording medium 50 includes, for example, a CD-ROM (Compact Disc Read Only Memory) or DVD-ROM (Digital Versatile Disc Read Only Memory), or a flash memory with a USB (Universal Serial Bus) connector.

In order for the computer 40 to function as the waveform analyzer 10, for example, a control program allowing the MPU 41 to perform various types of control processes as will be described below is created. The created control program is preliminarily stored in the hard disk device 44 or the portable recording medium 50. Moreover, the reference waveform data 16 and the tolerance information 17 should be preliminarily stored in the hard disk device 44. Furthermore, the A/D converter 30 should be connected to the interface device 47 of the computer 40, and the sampled data string of the waveform of an electrocardiogram signal output from the electrocardiogram sensor 20 should be ready for the computer 40 to read. Then, a specified instruction is given to the MPU 41 so as to read and execute the control program. Accordingly, it is possible for the computer 40 to provide the functions of the functional blocks provided for the waveform analyzer 10.

Alternatively, the waveform analyzer 10 may be configured by using a computer system comprised of a terminal device and a server device capable of transferring various types of data with the terminal device. In cases where the computer system functions as the waveform analyzer 10, the electrocardiogram sensor 20 and the A/D converter 30 are connected to a terminal device, and the server device includes, for example, the configuration of the computer 40 of FIG. 9. Note that the interface device 47 includes a communication device which manages the data communication with a communication device provided for the terminal device, and the terminal device transmits the sampled data string of the waveform of an electrocardiogram signal to the server device. On the other hand, the server device performs the control processes which will be described below according to the sampled data string received from the terminal device, and transmits the search result obtained in the control processes to the terminal device. Accordingly, it is possible to configure the waveform analyzer 10 by the above-described computer system.

Next, various types of control processes to be performed by the waveform analyzer 10 of FIG. 2 will be described.

Figure 10:
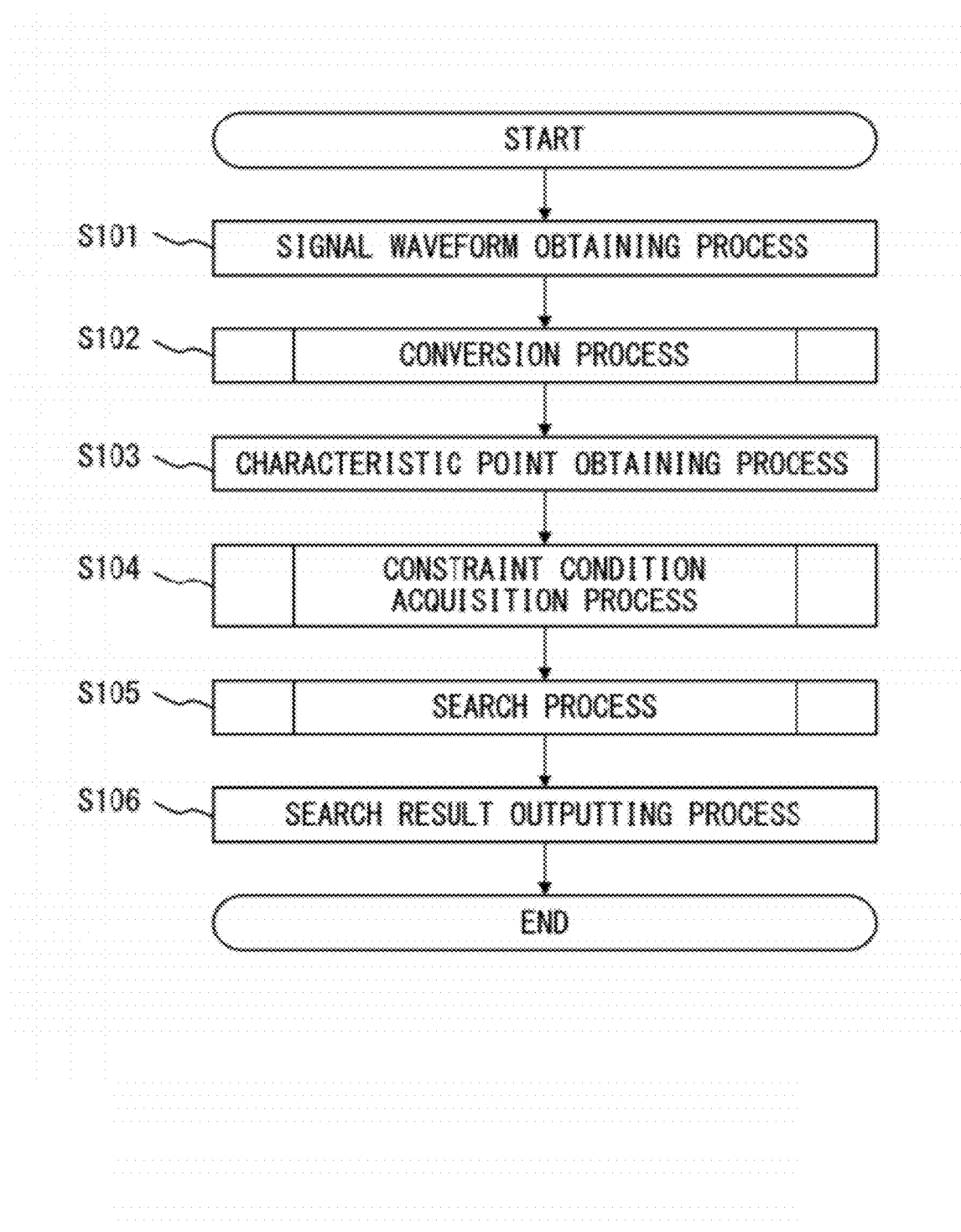
FIG. 10 is a flowchart illustrating how a waveform analysis process is performed.

Firstly, FIG. 10 will be described. FIG. 10 is a flowchart illustrating how a waveform analysis process is performed. The process starts when the waveform analyzer 10 detects a specified instruction for starting the process, which is given by an operator of the waveform analyzer 10.

In FIG. 10, firstly, the signal waveform obtaining unit 11 executes a signal waveform obtaining process in S101. In this process, a pair of data sets consisting of the paired data of a time obtained by sampling the signal waveform which indicates the signal waveform of an input signal and a value of the signal waveform at the time is obtained. In the present embodiment, in this process, the above-described pair of data sets indicating the electrocardiogram waveform, which is output from the A/D converter 30, is obtained.

Next, the converter 12 executes a conversion process in S102. In this process, a characteristic function where the paired data of a time and a value at that time is variable, which indicates the above-described signal waveform, is generated according to the above-described pair of data sets, and the generated characteristic function is converted into a second function, which is an expression on a BDD, and is output. The conversion process will be described later in detail.

Next, the characteristic point obtaining unit 13 executes a characteristic point obtaining process in S103. In this process, a setting instruction for a plurality of characteristic points, which are set on the reference waveform expressed in the reference waveform data 16, is obtained.

Next, the constraint condition acquisition unit 14 executes a constraint condition acquisition process in S104. In this process, the constraint condition for the relationship between time information specified by the characteristic points and a value corresponding to the time information in the above-described signal waveform, each of which are obtained in the characteristic point obtaining process of S103 for each of the characteristic points, is acquired. The constraint condition acquisition process will also be described later in detail.

Next, the searching unit 15 executes a search process in S105. In this process, the constraint condition acquired in the constraint condition acquisition process of S104 is applied to the characteristic function expressed in the BDD (second function) to obtain the time range which meets the constraint condition for all the characteristic points. The search process will also be described later in detail.

Next, the searching unit 15 executes a search result outputting process in S106. In this process, the time range obtained in the search process of S105 is output as a search result of the waveform analyzer 10. When the process of S106 is complete, the waveform analysis process of FIG. 10 ends.

The waveform analysis process consists of the processes described above.

Next, FIG. 11 will be described. FIG. 11 is a flowchart illustrating how the conversion process of S102 in FIG. 10 is performed.

In S111, the converter 12 firstly performs the process of creating a characteristic function as a Boolean function from the pair of data sets obtained in the signal waveform obtaining process of S101 in FIG. 10. In this process, firstly, time t and a value x at the time t are respectively expressed with n-levels and m-levels in binary (as a binary number), and the Boolean function $f(t_{n-1}, t_{n-2}, \ldots, t_1, t_0, x_{m-1}, x_{m-2}, \ldots, x_1, x_0)$ is created where the values of the levels are variable. Then, secondly, a process is performed so as to define that the value "1" will be returned when the pair of the time t and the value x included in the pair of data sets obtained in the signal waveform obtaining process of S101 in FIG. 10 corresponds to the value of the variable of the created Boolean function, and that the value "0" will be returned in the other cases. As a result, a characteristic function which represents the signal waveform of an input signal is created.

Next, in S112, the converter 12 performs the process of creating a directed graph which expresses the characteristic function created in S111.

Next, in S113, the converter 12 performs the process of obtaining the characteristic function, which represents the signal waveform of an input signal and is expressed in the BDD, by performing the above-described reduction process on the directed graph created in the process of S112. When the process of S113 is complete, the conversion process of FIG. 11 terminates. Then, the process returns to the waveform analysis process of FIG. 10.

The conversion process consists of the processes described above. The processes of S111, S112, and S113 which are performed by the converter 12 have been described above in detail. Here, the converter 12 may be configured to perform the process of creating a directed graph of S112 and the reduction process of S113 in parallel as described above such that a reduction process will be performed on a directed graph to which data is added every time the data of the characteristic function is added to the being-created directed graph.

Figure 12:
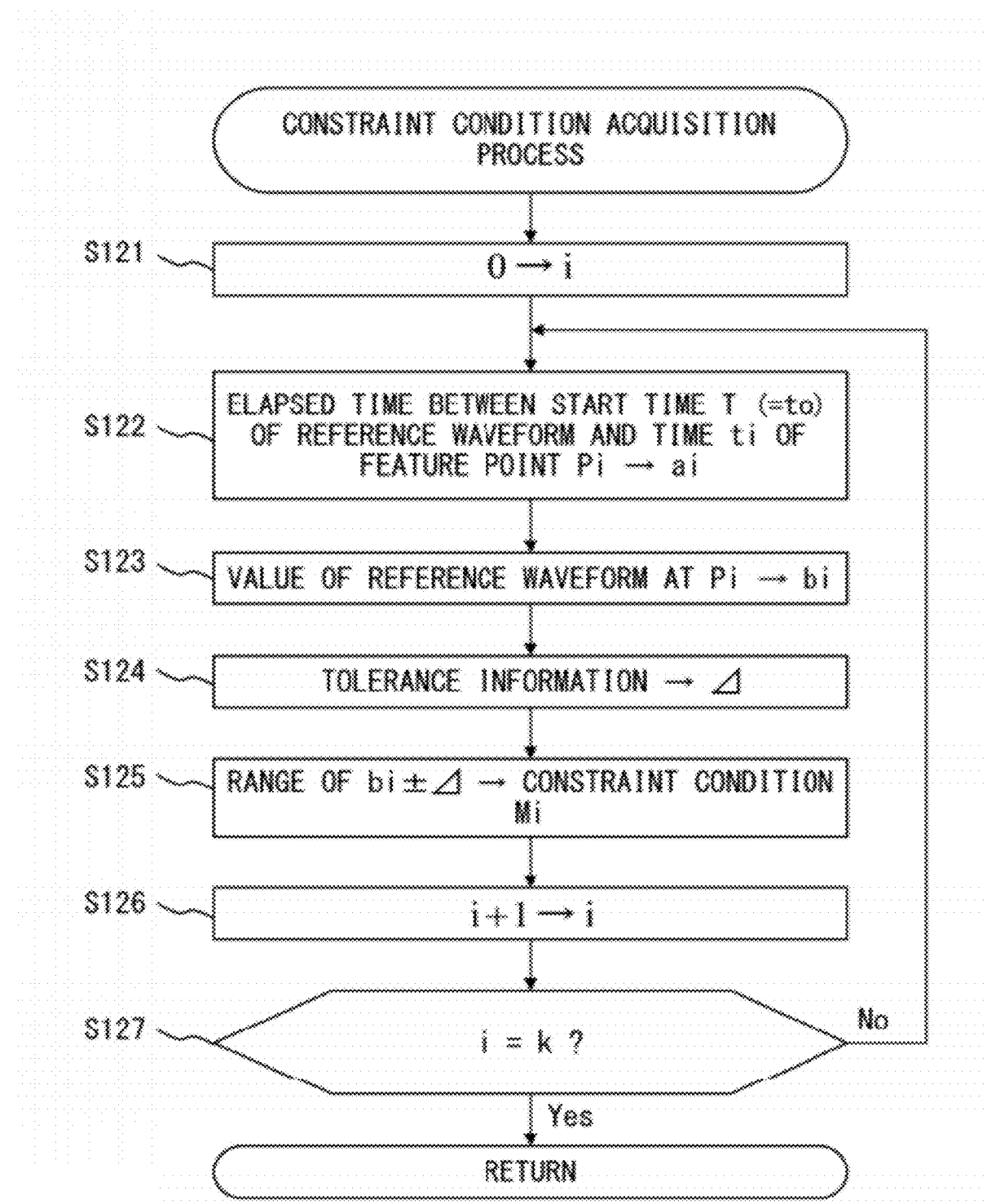
FIG. 12 is a flowchart illustrating how a constraint condition acquisition process is performed.

Next, FIG. 12 will be described. FIG. 12 is a flowchart illustrating how the constraint condition acquisition process of S104 in FIG. 10 is performed. In this process, it is assumed that the setting instructions have been obtained for the total of n number of characteristic points Pi (i=0, 1, ..., k−1) in the characteristic point obtaining process of S103 in FIG. 10.

In S121, the constraint condition acquisition unit 14 firstly performs the process of substituting the initial value "0" for the variable i.

Next, in S122, the constraint condition acquisition unit 14 performs the process of calculating the elapsed time between the start time T of a reference waveform expressed in the reference waveform data 16 and the time ti of the characteristic point Pi obtained in the characteristic point obtaining process in S103 of FIG. 10, and the process of substituting the calculated elapsed time for the variable ai.

Next, in S123, the constraint condition acquisition unit 14 performs the process of obtaining from the reference waveform data 16 the value of the reference waveform at the characteristic point Pi obtained in the characteristic point obtaining process of S103 in FIG. 10, and substituting the obtained value for the variable bi.

Next, in S124, the constraint condition acquisition unit 14 performs the process of obtaining the tolerance information 17, and substituting the obtained value of tolerance indicated in the information for the variable Δ.

Next, in S125, the constraint condition acquisition unit 14 performs the process of substituting information indicating the range of ±variable Δ about a current value of the variable bi for the variable Mi representative of the constraint condition.

Next, in S126, the constraint condition acquisition unit 14 performs the process of adding "1" to the current value of the variable i to update the value of the variable i.

Next, in S127, the constraint condition acquisition unit 14 performs the process of determining whether or not the current value of the variable i has reached the total number k of the characteristic points obtained in the characteristic point obtaining process of S103 in FIG. 10. Here, when it is determined that the value of the variable i has reached the total number k (when the determination result is "Yes"), the constraint condition acquisition process terminates. Then, the process returns to the waveform analysis process of FIG. 10. On the other hand, when it is determined that the value of the variable i has not reached the total number k (when the determination result is "No"), the constraint condition acquisition unit 14 returns the process to S122, and performs the above-described process on the variable i which was updated in the process of S126.

The constraint condition acquisition process consists of the processes described above. The processes of S122 through S125, which are performed by the constraint condition acquisition unit 14, have been described above in detail.

Figure 13:
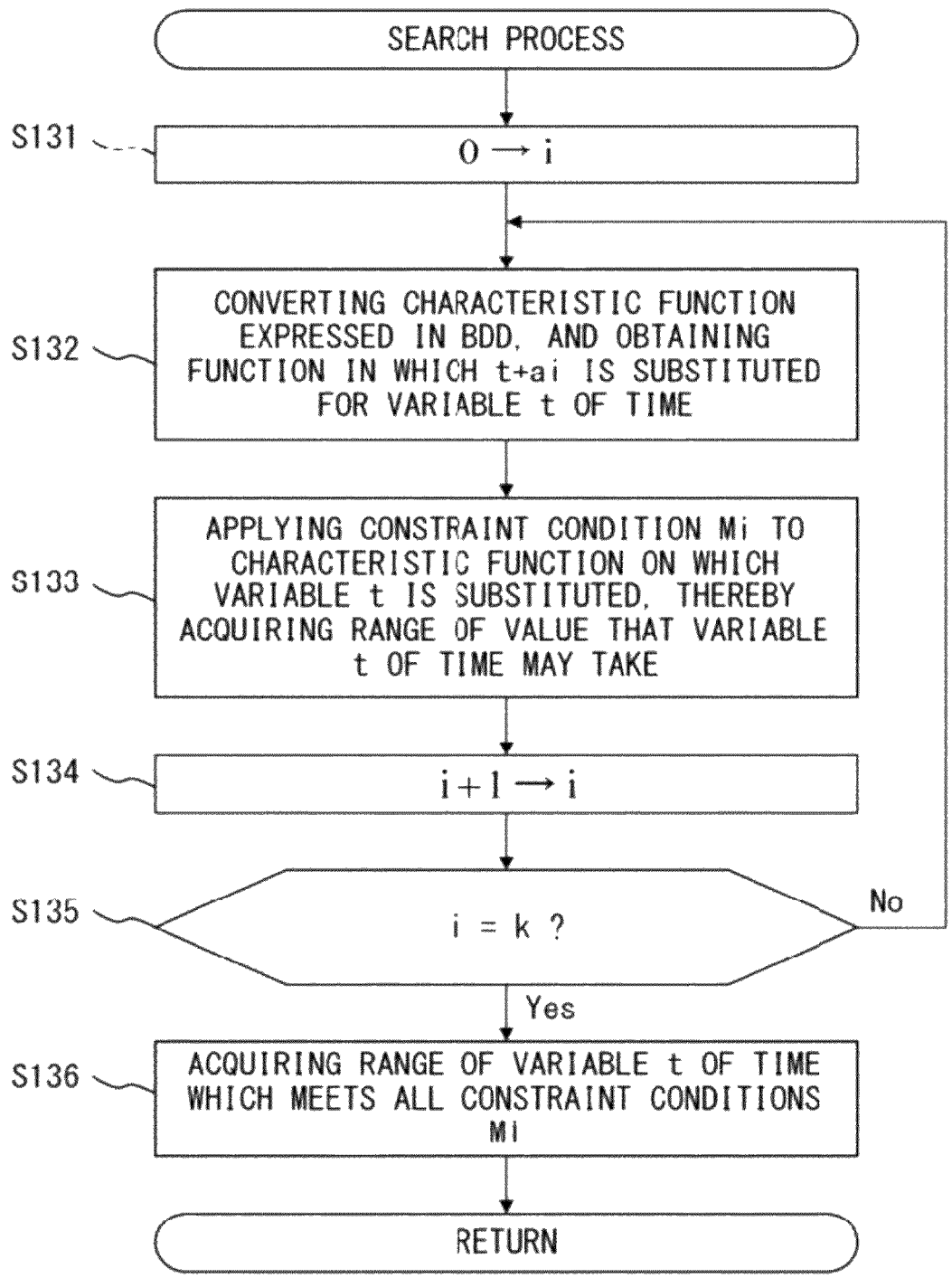
FIG. 13 is a flowchart illustrating a first example of how a search process is performed.

Next, FIG. 13 will be described. FIG. 13 is a flowchart illustrating a first example of how the search process of S105 in FIG. 10 is performed.

In S131, the searching unit 15 firstly performs the process of substituting the initial value "0" for the variable i.

Next, in S132, the searching unit 15 performs the process of converting the characteristic function expressed in the BDD, which is obtained in the process of S102 of FIG. 10, by using the above-described elapsed time ai obtained for the characteristic point Pi, and the process of obtaining a function in which t+ai is substituted for the variable t of the time in the function.

Next, in S133, the searching unit 15 performs the process of applying the constraint condition Mi to the characteristic function in which the variable t is substituted in the process of S132, and the process of acquiring the range of value that the variable t of the time may take in cases where the variable x takes a value within the range of bi±Δ.

Next, in S134, the searching unit 15 performs the process of adding "1" to the current value of the variable i to update the value of the variable i.

Next, in S135, the searching unit 15 performs the process of determining whether or not the current value of the variable i has reached the total number k of the characteristic points obtained in the characteristic point obtaining process of S103 in FIG. 10. Here, when it is determined that the value of the variable i has reached the total number k (when the determination result is "Yes"), the searching unit 15 shifts the process to S136. On the other hand, when it is determined that the value of the variable i has not reached the total number k (when the determination result is "No"), the searching unit 15 returns the process to S132, and performs the above-described process on the variable i which was updated in the process of S134.

Next, in S136, the searching unit 15 performs the process of acquiring the range of the variable t of the time which meets all the constraint conditions Mi, i.e., the process of acquiring the time range which is entirely included in the range of values that the variable t of the time may take, which is obtained each time the process of S133 is repeated. When the process of S136 is complete, the conversion process of FIG. 13 terminates, and the process then returns to the waveform analysis process of FIG. 10. Subsequently, the time range acquired in the process of S136 is output in the search result outputting process of S106 as a search result of the waveform analyzer 10.

The search process consists of the processes described above.

As various types of control processes are performed in the waveform analyzer 10 of FIG. 2 as described above, it becomes possible for the waveform analyzer 10 to search a similar portion between the signal waveform of an input signal and the reference waveform.

The above-described operation of the waveform analyzer 10 may be modified in a variety of ways, as will be described below.

For example, in the search process illustrated in FIG. 13, firstly, in the process of S132, a variable replacement operation, which corresponds to the time difference between the time specified by the characteristic point and the reference time preliminarily set for the reference waveform, is performed on the characteristic function expressed in the BDD. Then, in the process of S133, the constraint condition obtained for the characteristic points is applied to the characteristic function on which the variable replacement operation is performed, thereby acquiring the time which meets the constraint condition for the characteristic point. Here, the order may be changed.

Figure 14:
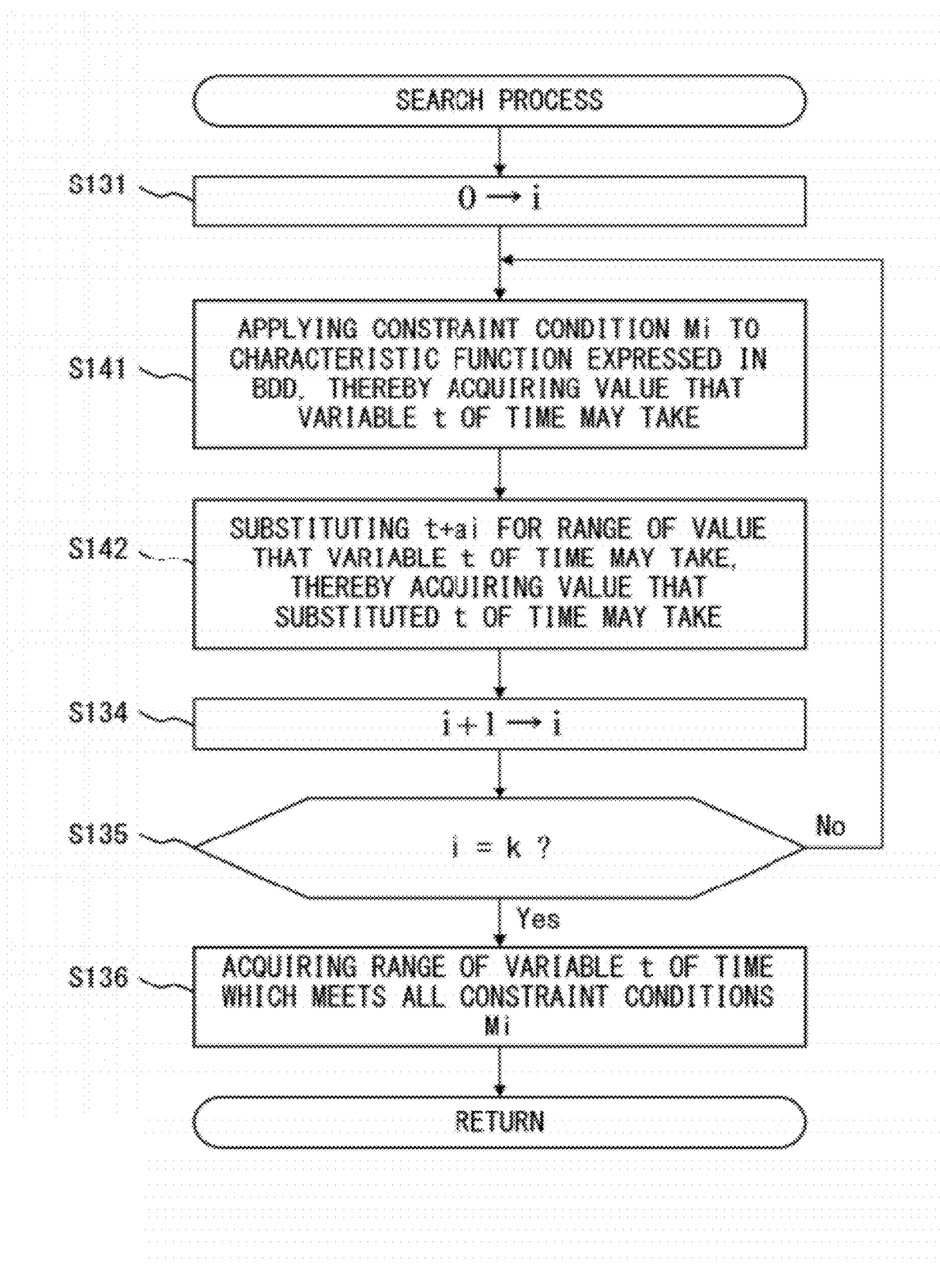
FIG. 14 is a flowchart illustrating a second example of how a search process is performed.

Here, FIG. 14 will be described. FIG. 14 is a flowchart illustrating a second example of how the search process of S105 in FIG. 10 is performed.

In the processes illustrated in FIG. 14, the processes of S141 and S142 are substituted for the processes of S132 and S133 out of the processes illustrated in FIG. 13. For this reason, only the processes of S141 and S142 will be described here.

In the process of S141 subsequent to S131, the searching unit 15 performs the process of applying the constraint condition Mi to the characteristic function expressed in the BDD which is obtained in the process of S102 of FIG. 10, thereby acquiring the range of values that the variable t of the time may take in cases where the variable x takes a value within the range of bi±Δ.

Next, in S142, the searching unit 15 performs the process of substituting t+ai for the range of values that the variable t of the time obtained in the process of S141 may take by using the above-described elapsed time ai obtained for the characteristic point Pi, thereby acquiring the range of values that the substituted t may take. Subsequent to the completion of this process, the searching unit 15 moves the process to S134.

As described above, in the process of FIG. 14, the searching unit 15 firstly applies for each of the characteristic points the constraint condition obtained for the characteristic points to the characteristic function expressed in the BDD. Then, the searching unit 15 performs a variable replacement operation, which corresponds to the time difference between the time specified by the characteristic points and the reference time preliminarily set for the reference waveform, on the time range which meets the constraint condition. As described above, if the constraint condition is applied to the characteristic function expressed in the BDD before the variable replacement operation which corresponds to the time difference, the size of the BDD (i.e., the number of nodes) is reduced. Accordingly, a reduction in the amount of computation in the subsequent variable replacement operation is expected.

In the constraint condition acquisition process illustrated in FIG. 12, for example, it may be configured such that the constraint condition Mi will be converted into an expression on a BDD. Moreover, in the search process illustrated in FIG. 13, for example, it may be configured such that the constraint condition Mi expressed in the BDD will also be converted into the characteristic function expressed in the BDD.

Figure 15A:
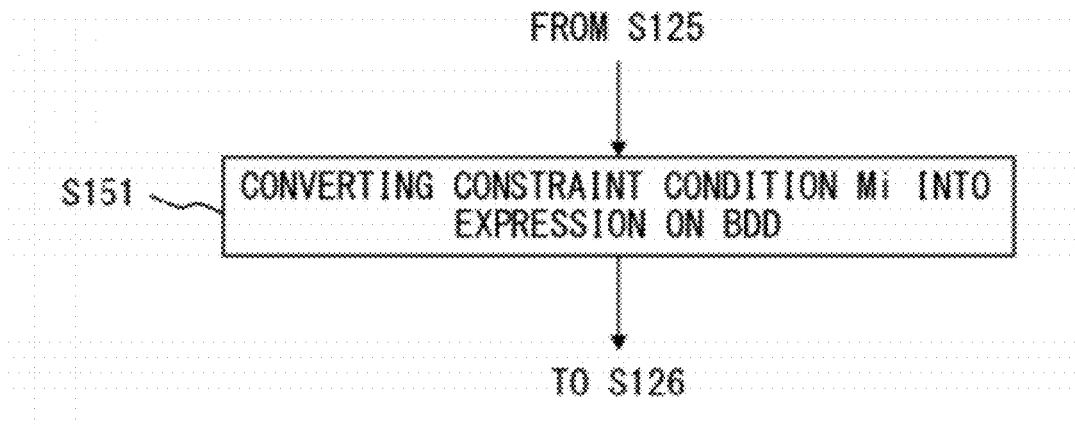
FIG. 15A illustrates a variation of the flowchart of FIG. 12.
Figure 15B:
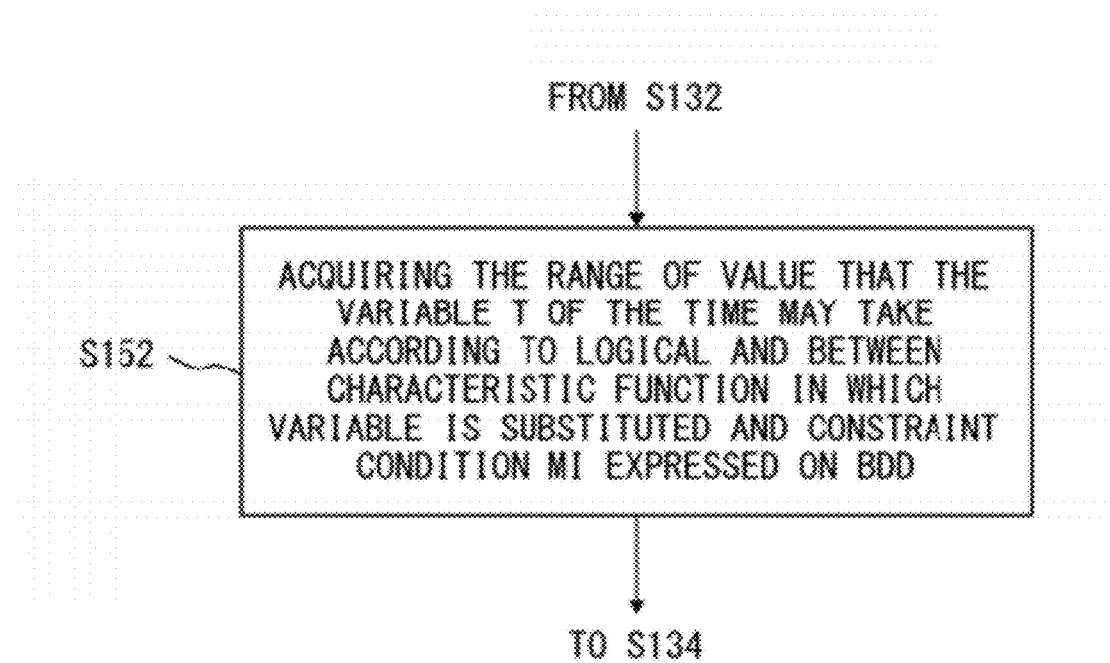
FIG. 15B illustrates a first variation of the flowchart of FIG. 13.

Here, FIGS. 15A and 15B will be described. FIG. 15A is a variation of the flowchart of FIG. 12, and FIG. 15B is a first variation of the flowchart of FIG. 13. In these variations, the above-described operations are performed by the constraint condition acquisition unit 14 and the searching unit 15.

Firstly, the process of S151 in FIG. 15A is performed between the processes of S125 and S126 in FIG. 12.

In S151, the constraint condition acquisition unit 14 performs the process of converting the constraint condition Mi obtained in the process of S125 in FIG. 12 into an expression on a BDD, and moves the process to S126 of FIG. 12.

Here, a technique for expressing the constraint condition by using a BDD will be described with reference to FIG. 16.

Figure 16:
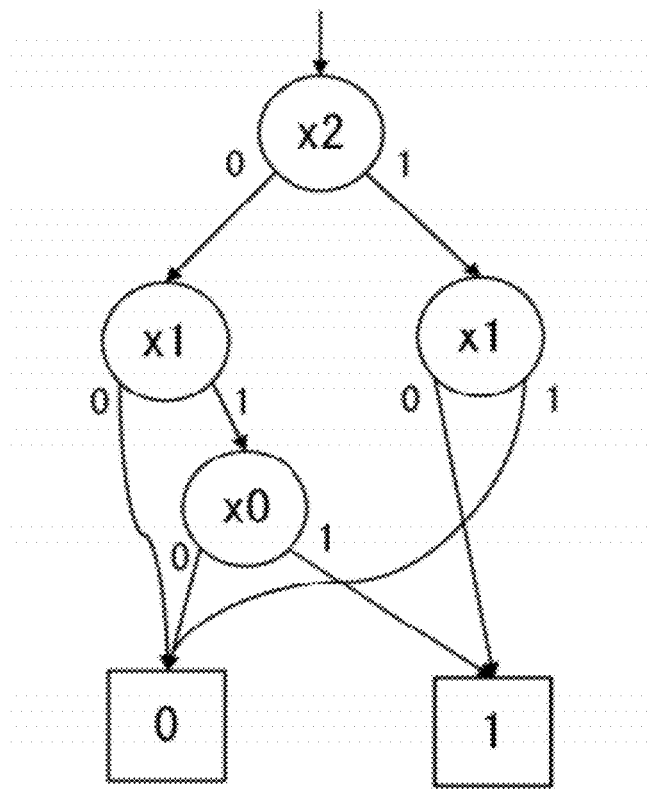
FIG. 16 is a diagram illustrating a technique for expressing a constraint condition by using a BDD.

In the example of FIG. 16, the value of the reference waveform bi in the characteristic point Pi is "4", and the constraint condition Mi of when the tolerance Δ is "1" is expressed by using a BDD. In this case, the constraint condition Mi for the variable x is that x is in the range of "4"±"1", which is equivalent to the condition that the value of x is 3≤x≤5.

Here, if the variable x is expressed with three levels of binary (x2, x1, x0), the constraint condition Mi may be expressed as a characteristic function f(x2, x1, x0), where the value "1" is returned only when (x2, x1, x0) is one of (0, 1, 1), (1, 0, 0), and (1, 0, 1), and the value "0" is returned in the other cases. If the directed graph representative of this characteristic function is created and a reduction process is performed on the created directed graph, the BDD illustrated in FIG. 16 as an example is obtained. Also in this case, the creation of a directed graph of the characteristic function representative of the constraint condition Mi and its reduction process may be performed in parallel, as described above.

On the other hand, the process of S152 in FIG. 15B is performed instead of the process of S133 in FIG. 13.

In S152, the searching unit 15 firstly performs the logical AND operation process between the characteristic function in which the variable t is substituted in the process of S132 of FIG. 13 and the constraint condition Mi expressed on the BDD obtained in the process of S151 of FIG. 15A. Secondly, the searching unit 15 performs the process of acquiring the range of value that the variable t of the time may take (the set of time t at which f'=1) from the characteristic function f' obtained in the logical AND operation. Then, the searching unit 15 moves the process to S134 of FIG. 13.

As described above, in the process of FIG. 15A, the constraint condition acquisition unit 14 creates a BDD representing the constraint condition according to the value of the reference waveform at the characteristic points and the specified tolerance. Moreover, in the process of FIG. 15B, the searching unit 15 applies the constraint condition to the characteristic function by performing a logical AND operation between the characteristic function expressed in the BDD and a BDD representing the constraint condition. As described above, if the constraint condition is expressed in a BDD, it is possible to apply the constraint condition to the characteristic function in the logical operation on the BDD. Accordingly, the operational efficiency for the application improves, and as a result, the efficiency in the process of pattern matching further improves.

Moreover, the constraint conditions Mi acquired by the constraint condition acquisition unit 14 may be, for example, constraints on the maximum value, minimum value, or average value of the value of the signal waveform of an input signal within the specified period t±Δt around the time t specified by the characteristic point Pi.

Figure 17:
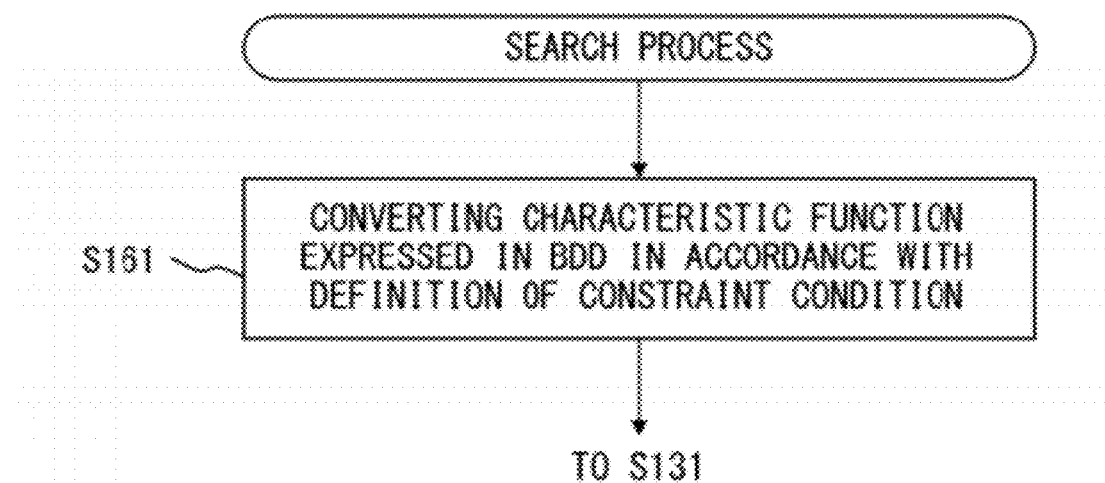
FIG. 17 illustrates a second variation of the flowchart of FIG. 13.

Here, FIG. 17 will be described. FIG. 17 is a second variation of the flowchart of FIG. 13. This variation is designed such that the searching unit 15 will perform the process when the constraint condition Mi represents constraints on the above-described maximum value, minimum value, or average value.

The process of S161 in FIG. 17 is a process to be performed at the beginning of the search process of FIG. 13.

In S161, the searching unit 15 performs the process of converting the characteristic function expressed in the BDD, which is obtained in the process of S102 of FIG. 10, in accordance with the definition of the constraint condition Mi, and then moves the process to S131 of FIG. 13.

In the process of S161, when the constraint condition Mi represents constraints on the above-described maximum value, minimum value, or average value, the characteristic functions expressed in the BDD f(t, x) are converted into f'(t, x) expressed in Equation 2, respectively.

Case of Maximum Value $f'(t, x) = \max_{-\Delta t \leq j \leq +\Delta t} [f(t+j, x)]$  Equation 2

Case of Minimum Value $f'(t, x) = \min_{-\Delta t \leq j \leq +\Delta t} [f(t+j, x)]$ Case of Maximum Value $f'(t, x) =$ $$\frac{1}{2\Delta t + 1} \sum_{-\Delta t \leq j \leq +\Delta t} f(t+j, x)$$

The conversion of the characteristic function expressed in the BDD f(t, x) into f'(t, x) of Equation 2 is easily achieved by applying the calculation of BDD thereto.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A waveform analyzer which searches a signal waveform of an input signal for a portion similar to a reference waveform, the waveform analyzer comprising a computer that includes:
   an electrocardiogram sensor which measures an action potential of cardiac muscle and which outputs an electrocardiogram signal; and
   a processor which performs a process including:
      a signal waveform obtaining process which obtains a pair of data sets of a time and a value of the signal waveform of the electrocardiogram signal, which is outputted from the electrocardiogram sensor, at the time obtained by sampling the signal waveform;
      a convert process which creates according to the pair of data sets a characteristic function which is a logical function where a pair of data including a time and a value at the time is variable, and which converts the created characteristic function into a second function which is an expression on a binary decision diagram;
      a constraint condition acquisition process which obtains for each of characteristic points of the reference waveform a constraint condition representative of constraints on a relationship between time information specified by the characteristic points and a value corresponding to the time information in the signal waveform according to a value of the reference waveform at the characteristic points and a specified tolerance given to a value of the reference waveform by creating a binary decision diagram representing the constraint condition according to the value of the reference waveform at the characteristic points and the specified tolerance; and a searching process which applies the constraint condition for each of the plurality of characteristic points to the second function to obtain a time range which meets the constraint condition for all the plurality of characteristic points, and which outputs information of the time range as a result of a search, the constraint condition being applied by performing a logical operation between the binary decision diagram representing the second function and the binary decision diagram representing the constraint condition.

2. The waveform analyzer according to claim 1, wherein the searching process firstly performs on the second function for each of the characteristic points a variable replacement operation, which corresponds to a time difference between a time specified by the characteristic points and a reference time preliminarily set for the reference waveform, and subsequently applies the constraint condition obtained for the characteristic points to the characteristic function on which the variable replacement operation is performed to calculate the time range which meets the constraint condition for the characteristic points.

3. The waveform analyzer according to claim 1, wherein the searching process applies to the second function for each of the characteristic points the constraint condition obtained for each of the characteristic points to calculate the time range which meets the constraint condition for the characteristic points, and subsequently performs a variable replacement operation, which corresponds to a time difference between a time specified by the characteristic points and a reference time preliminarily set for the reference waveform, on the time range which meets the constraint condition.

4. The waveform analyzer according to claim 1, wherein the convert process creates a function as the characteristic function where elements of paired data are expressed in binary and values of levels are variable, and returns a value "1" when a value included in the pair of data sets corresponds to a value of the variable and returns a value "0" when a value not included in the pair of data sets corresponds to the value of the variable.

5. The waveform analyzer according to claim 1, wherein the constraint condition represents constraints on a maximum amplitude value of the signal waveform in a specified period around a time specified by the characteristic point.

6. The waveform analyzer according to claim 1, wherein the constraint condition represents constraints on a minimum amplitude value of the signal waveform in a specified period around a time specified by the characteristic point.

7. The waveform analyzer according to claim 1, wherein the constraint condition represents constraints on an average amplitude value of the signal waveform in a specified period around a time specified by the characteristic point.

8. A method of performing a search on a signal waveform of an input signal for a portion similar to a reference waveform, the method comprising:

obtaining an electrocardiogram signal from an electrocardiogram sensor which measures an action potential of cardiac muscle and which outputs the electrocardiogram signal;

creating a characteristic function which is a logical function where a pair of data including time and a value at the time is variable according to a pair of data sets including a time and a value of the signal waveform of the electrocardiogram signal, which is outputted from the electrocardiogram sensor, at the time obtained by sampling the signal waveform, and converting the created characteristic function into a second function which is an expression on a binary decision diagram;

obtaining for each of characteristic points of the reference waveform a constraint condition representative of constraints on a relationship between time information specified by the characteristic points and a value corresponding to the time information in the signal waveform according to a value of the reference waveform at the characteristic points and a specified tolerance given to a value of the reference waveform by creating a binary decision diagram representing the constraint condition according to the value of the reference waveform at the characteristic points and the specified tolerance; and applying the constraint condition for each of the plurality of characteristic points to the second function to obtain a time range which meets the constraint condition for all the plurality of characteristic points, and then acquiring information of the time range as a result of a search, the constraint condition being applied by performing a logical operation between the binary decision diagram representing the second function and the binary decision diagram representing the constraint condition.

9. A computer readable non-transitory recording medium on which a program is recorded to allow a computer to execute a process of performing a search on a signal waveform of an input signal for a portion similar to a reference waveform, the program comprising:

obtaining an electrocardiogram signal from an electrocardiogram sensor which measures an action potential of cardiac muscle and which outputs the electrocardiogram signal;

creating a characteristic function which is a logical function where a pair of data including time and a value at the time is variable according to a pair of data sets including a time and a value of the signal waveform of the electrocardiogram signal, which is outputted from the electrocardiogram sensor, at the time obtained by sampling the signal waveform, and converting the created characteristic function into a second function which is an expression on a binary decision diagram;

obtaining for each of characteristic points of the reference waveform a constraint condition representative of constraints on a relationship between time information specified by the characteristic points and a value corresponding to the time information in the signal waveform according to a value of the reference waveform at the characteristic points and a specified tolerance given to a value of the reference waveform by creating a binary decision diagram representing the constraint condition according to the value of the reference waveform at the characteristic points and the specified tolerance; and applying the constraint condition for each of the plurality of characteristic points to the second function to obtain a time range which meets the constraint condition for all the plurality of characteristic points, and then acquiring information of the time range as a result of a search, the constraint condition being applied by performing a logical operation between the binary decision diagram representing the second function and the binary decision diagram representing the constraint condition.

10. The waveform analyzer according to claim 1, wherein the logical operation is a logical AND operation.

11. The method according to claim 8, wherein the logical operation is a logical AND operation.

12. The computer readable non-transitory recording medium according to claim 9, wherein the logical operation is a logical AND operation.

* * * * *